(12) United States Patent
Kim

(10) Patent No.: US 6,511,318 B2
(45) Date of Patent: *Jan. 28, 2003

(54) DENTAL ARTICULATOR

(75) Inventor: Yunsoon Kim, Farmington, CT (US)

(73) Assignee: Nu-Tek Dental, LLC, East Windsor, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/988,311

(22) Filed: Nov. 19, 2001

(65) Prior Publication Data

US 2002/0031743 A1 Mar. 14, 2002

Related U.S. Application Data

(63) Continuation-in-part of application No. 09/287,133, filed on Apr. 7, 1999, now Pat. No. 6,318,999, which is a continuation-in-part of application No. 09/964,482, filed on Sep. 28, 2001.

(30) Foreign Application Priority Data

Jul. 21, 2001 (KR) .............. 10-2001-0043968

(51) Int. Cl.⁷ .............................................. A61L 19/00
(52) U.S. Cl. .............................. 433/74; 433/64; 433/60
(58) Field of Search .............................. 433/49, 50, 53, 433/54, 57, 60, 61, 62, 64, 66, 67, 74

(56) References Cited

U.S. PATENT DOCUMENTS

| | | |
|---|---|---|
| 981,430 A | 1/1911 | Kennedy |
| 1,736,006 A | 11/1929 | Hagman |
| 2,619,725 A | 12/1952 | Roeser |
| 2,786,272 A | 3/1957 | Lindley |
| 3,937,773 A | 2/1976 | Huffman |
| 3,965,576 A | 6/1976 | Eveland |
| 4,021,916 A | 5/1977 | Spalten |
| 4,022,419 A | 5/1977 | Haker |
| 4,163,319 A | 8/1979 | Ouaknine |
| 4,265,619 A | 5/1981 | Lucki et al. |
| 4,382,787 A | 5/1983 | Huffman |
| 4,398,884 A | 8/1983 | Huffman |

(List continued on next page.)

OTHER PUBLICATIONS

"Vertex Articulating System Instructions" (Pamphlet), Ceramco, pp. 1–8, Burlington, New Jersey, U.S.A.; Weybridge, Surrey, United Kingdom, 1997.
"Artiquick System Instructions for Use", Dental Ventures of America, Inc., Corona, California, U.S.A.
"Just Wing It Articulators", instructional handout.
"Die–Maker W.O.O. Articulator Instructions".
"Catalog of Articulators", LMT, pp. 29–36, Apr. 1994.
"Ballox Instructions", Shebah Dental Products, Inc., La Habra, California, U.S.A.

*Primary Examiner*—Ralph A. Lewis
(74) *Attorney, Agent, or Firm*—Birch, Stewart, Kolasch & Birch, LLP

(57) ABSTRACT

A dental modeling system includes a pair of supports for opposing dental casts which are articulated together by a pair of pivotally connected articulator arms. The support may include a plurality of integral registration pins extending from a top surface thereof which provide superior registration of a dental casts located thereon. The support may be directly attached to the articulator arm, or may be attached via a ball-and-socket joint, which, once located in the proper position, is glued in place. The articulator arm permits the castings to move toward and away from one another, and permits the replication of centric, excursive, and protrusive movements of the jaw. An alternative support for a dental cast includes a back member and a bottom member oriented at approximately 90° with respect to one another to form an L-shaped main body, onto which a dental cast may be attached.

27 Claims, 19 Drawing Sheets

U.S. PATENT DOCUMENTS

| | | |
|---|---|---|
| 4,439,151 A | 3/1984 | Whelan |
| 4,449,930 A | 5/1984 | Huffman |
| 4,449,931 A | 5/1984 | Saito |
| 4,451,234 A | 5/1984 | Oye |
| 4,481,162 A | 11/1984 | Huffman |
| 4,508,506 A | 4/1985 | Jackson |
| 4,533,323 A | 8/1985 | Huffman |
| 4,538,987 A | 9/1985 | Weissman |
| 4,548,581 A | 10/1985 | Huffman |
| 4,608,016 A | 8/1986 | Zeiser |
| 4,708,648 A | 11/1987 | Weissman |
| 4,721,464 A | 1/1988 | Roden et al. |
| 4,734,033 A | 3/1988 | Huffman |
| 4,767,330 A | 8/1988 | Burger |
| 4,786,253 A | 11/1988 | Morais |
| 4,842,242 A | 6/1989 | Huffman |
| 4,842,515 A | 6/1989 | Zeiser |
| 4,898,359 A * | 2/1990 | Gopon .................. 433/74 |
| 4,957,435 A | 9/1990 | Jinoian et al. |
| 5,129,822 A | 7/1992 | Dobbs |
| 5,197,874 A | 3/1993 | Silva et al. |
| 5,232,365 A | 8/1993 | Ikehara |
| 5,286,191 A | 2/1994 | Poveromo |
| 5,306,145 A | 4/1994 | Michael |
| 5,360,337 A | 11/1994 | Westdyk |
| 5,403,185 A | 4/1995 | Presswood |
| 5,425,636 A | 6/1995 | Ghim |
| 5,466,152 A | 11/1995 | Walter |
| 5,506,095 A | 4/1996 | Callne |
| 5,622,497 A | 4/1997 | Cho |
| 5,658,143 A | 8/1997 | Kuperman |
| 5,766,007 A | 6/1998 | Huffman |
| 5,769,634 A | 6/1998 | Choi |
| 5,775,899 A | 7/1998 | Huffman |
| 5,788,489 A | 8/1998 | Huffman |
| 5,807,102 A | 9/1998 | Lang et al. |
| 5,846,076 A | 12/1998 | Garland |
| 5,957,688 A | 9/1999 | Van Valey |
| 6,089,863 A | 7/2000 | Van Valey |
| 6,106,284 A | 8/2000 | Cronin et al. |
| D430,672 S | 9/2000 | Huffman |
| 6,318,999 B1 * | 11/2001 | Kim .......................... 433/74 |

* cited by examiner

DENTAL ARTICULATOR

This application is a Continuation-in-Part of prior copending application Ser. No. 09/287,133, filed Apr. 7, 1999, now U.S. Pat. No. 6,318,999 and prior copending application Ser. No. 09/964,482, filed Sep. 28, 2001, the entire contents of both of which are hereby incorporated by reference.

BACKGROUND OF THE INVENTION

1. Field of the Invention

The present invention relates to dental articulators which permit a pair of opposing dental casts to be repeatedly positioned adjacent one another and moved away from one another for the preparation of dental prosthesis elements such as crowns, bridges, caps, etc. More particularly, the present invention is directed to a dental modeling system including supports for dental casts, and to an inexpensively formed articulator which permits replication of centric, excursion and protrusive movements while still allowing proper registration of the maxillary and mandibular dental casts.

2. Background of the Invention

Various dental articulators are known in the art to which a pair of dental casts are mounted which simulate the movement of the human jaw. Typically, dental articulators are utilized by dentists or dental technicians to create an accurately fitting dental prosthesis, such as a crown, bridge, or cap. Dental articulators are used to mount castings of a patient's teeth which are used as a model for the creation of the dental prosthesis. In preparing the dental casts, a dentist normally makes a negative impression of the patient's teeth, which may be a partial or full arch impression. This negative impression serves as a mold for developing a casting of the patient's teeth. The negative impression is filled with a pourable casting stone which is allowed to harden and thereby form a replica of the patient's teeth. The upper and lower castings may then be attached to an articulator which allows the opposing casts to be moved toward or away from one another.

Typically, the dental technician will be working on one tooth or several teeth in one of the dental casts. Therefore, it is necessary for the dental technician to separate the tooth from the rest of the dental cast. This separation is performed by sawing through the casting on opposite sides of the tooth. However, doing so separates the tooth from the remainder of the casting which creates a problem when repositioning the tooth with respect to the remainder of the dental cast.

In order to perform such repositioning, previous methods have been developed whereby one or more pins are inserted into a lower surface of the portion of the dental cast containing the single tooth, and corresponding holes are placed in the base of the remaining portion of the dental cast. However, the requirement for the provision of pins and holes requires additional labor, thereby increasing costs and slowing the process. Further, this method does not necessarily lead to an accurate re-registration of the single tooth with respect to the remaining portion of the dental cast. This technique wherein the model is poured, allowed to harden, then cut into dies, and is then pindexed into another base is known as "a dry pinning technique."

Another method known as "a wet pinning technique" utilizes a tray support member having a plurality of holes therein into which several indexing pins are placed. The tray support member and the indexing pins are then covered with casting material which is either poured directly onto the tray support member, or alternatively, into the negative impression taken by the dentist. The negative impression is then placed over the tray support member and allowed to harden. Once the casting material is hardened, the hardened casting material may be removed from the tray support member with the indexing pins being retained in the casting material. The model may be cut into segmented pieces and returned to the tray support member by placing the segmented portions with their indexing pins back into the indexing holes from which they were taken.

The castings or tray support members may be attached to articulator arms for moving the castings toward and away from one another. However, present commercially available articulators for wet pinning systems are flimsy and do not permit reliable registration of the upper and lower castings with respect to one another. Also, the tray support member onto which the casting stone is poured does not allow positive, accurate, and solid re-registration of a segmented tooth onto the tray support member, thus resulting in improper spatial relationship of the segmented tooth with respect to the remainder of the dental cast, which can result in the formation of an improperly fitting crown, cap, or bridge. Correcting such an improperly fitting dental prosthesis unnecessarily increases the amount of labor, costs, material, and patient's time in the office or lab.

There is a need in the art for a simple dental articulator which allows better stabilization of the prosthesis element being worked on, without shifting, or movement of the prosthesis dies in the lab while being worked on. There is also a need in the art for a dental articulator which provides accurate registration of the mandibular and maxillary quadrants or arches of a patient's mouth, while also permitting recreation of the jaw movements of the patient in centric, excursive, and protrusive manners.

The current invention addresses the dichotomy of the "dry pinning" vs. wet pinning technique. Historically the dry pinning technique has been accurate but very labor intensive and time consuming. Conversely, the wet pinning technique has been less labor intensive but not as accurate. The current invention addresses both. The truncated pyramids and the tapered and appropriately sized holes, (pins optional) make for an extremely accurate repositioning of the casts. The elimination of separate casts and the need for time consuming pindexing is eliminated.

Another object of the present invention is to provide a dental modeling system which permits the castings to be produced and articulated in the most economical fashion, both in cost and time required to produce an articulated model of a patient's teeth. Another problem addressed and solved is that of using quickly setting cyanoacrylate glue. The glue slot and glue hole of the invention prevent unnecessary glue from flowing into and onto undesired areas, and therefore reduces the need for cleanup. In particular, skin contact with the glue is prevented.

SUMMARY OF THE INVENTION

The above and other objects of the present invention are obtained by a dental modeling system comprising a support for a dental cast, the support including a main body having a top surface and a plurality of registration pins extending upwardly from the top surface, the registration pins being formed integrally with the main body as a one-piece unit, the registration pins each having a pyramidal shape with four sides which taper inwardly extending away from the top surface of the main body. The support may also include one or more apertures located in the top surface of the main body and extending therein. This and another support may include or be attached to an articulator including a first articulator arm having a first hinged portion, a second articulator arm having a second hinged portion pivotally connected to the first hinged portion of the first articulator arm, with one support attached to the first articulator arm for supporting a first dental cast and a second support attached to the second articulator arm for supporting a second dental cast. This support may be used as part of a wet pinning system as described above wherein the casting stone is placed on the support while in the viscous state and allowed to harden on the support.

The articulator of the present invention may be utilized with previously formed and hardened casts (available by different manufacturers) by utilizing an alternative support including a back member and a bottom member which together form an L-shaped main body, with the back member being oriented at approximately 90° with respect to the bottom member. The support may be fastened to the previously formed and hardened dental cast by using an appropriate fastener, such as cryanoacrylic glue. Alternatively, the casting may be formed directly onto the L-shaped main body portion, for example, in instances where it will not be necessary to segment the casting into separate elements.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
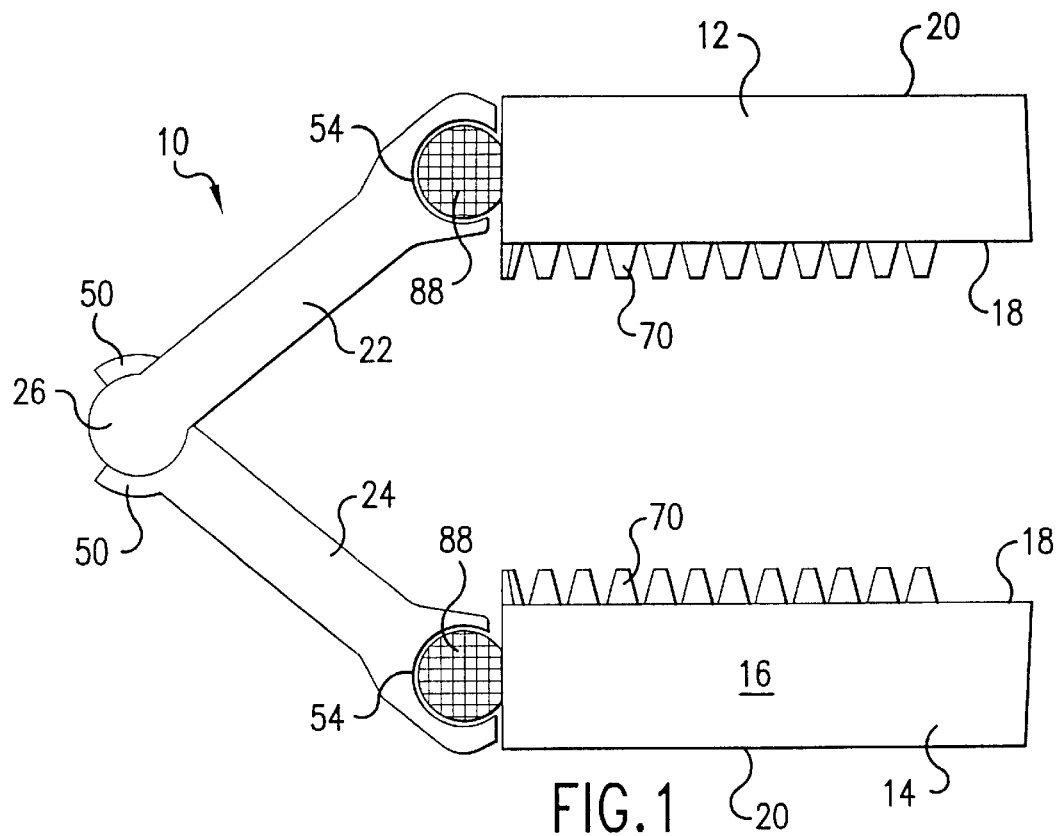
FIG. 1 is a side view of the dental articulator according to a first embodiment.

A dental modeling system 10 according to the present invention will now be described with reference to FIGS. 1–39. FIG. 1 shows a first embodiment of the dental modeling system 10. In the first embodiment, an upper support 12 is arranged in an opposing relationship with respect to a lower support 14. Although the upper support 12 and lower support 14 are shown as quadrants in most of the Figures, it should be understood that full arches may be utilized as shown in FIGS. 26, 27 and 31–36. In FIG. 1, the upper support 12 is identical to the lower support 14, and therefore, discussion will be made with respect to the lower support 14 with the understanding that the same description applies to the upper support 12. The lower support 14 includes a main body 16 which has a block-like external configuration. The main body 16 has an upper surface 18 and a lower surface 20. The upper surface 18 is configured to support a dental cast C thereon. A more detailed discussion of the lower support 14 will follow.

The upper support 12 is attached to a first articulator arm 22, and the lower support 14 is attached to a second articulator arm 24. The first articulator arm 22 and the second articulator arm 24 are pivotally interconnected together by a hinge 26. The hinge 26 allows the first articulator arm 22 to pivot with respect to the second articulator arm 24, thus causing the upper support 12 to be movable toward and away from the lower support 14. Thus, with a dental cast C attached to both the upper support 12 and the lower support 14, it is possible to simulate the opening and closing movement of a patient's teeth with the dental modeling system 10.

The articulator arms of the present invention will now be described in detail, with particular reference to FIGS. 2–6. The first articulator arm 22 is identical to the second articulator arm 24. Thus, the production of only one articulator arm is necessary for use with the dental modeling system 10 of the present invention. The following description will be made with respect to the first articulator arm 22, with the understanding that the same description applies to the second articulator arm 24. The first articulator arm 22 includes a pair of spaced apart arms 28. One end of each of the arms 28 is connected to a first cross-member 30 and the other end of each of the arms 28 is connected to a second cross-member 32. The arms 28 have a cross-section wherein the height (as viewed in FIG. 3) is approximately twice as large as the width (as viewed in FIG. 4). This permits the articulator arm 22 to be more susceptible to favorable lateral deflection (as viewed in FIG. 4) than unfavorable vertical deflection (as viewed in FIG. 3).

Figure 4:
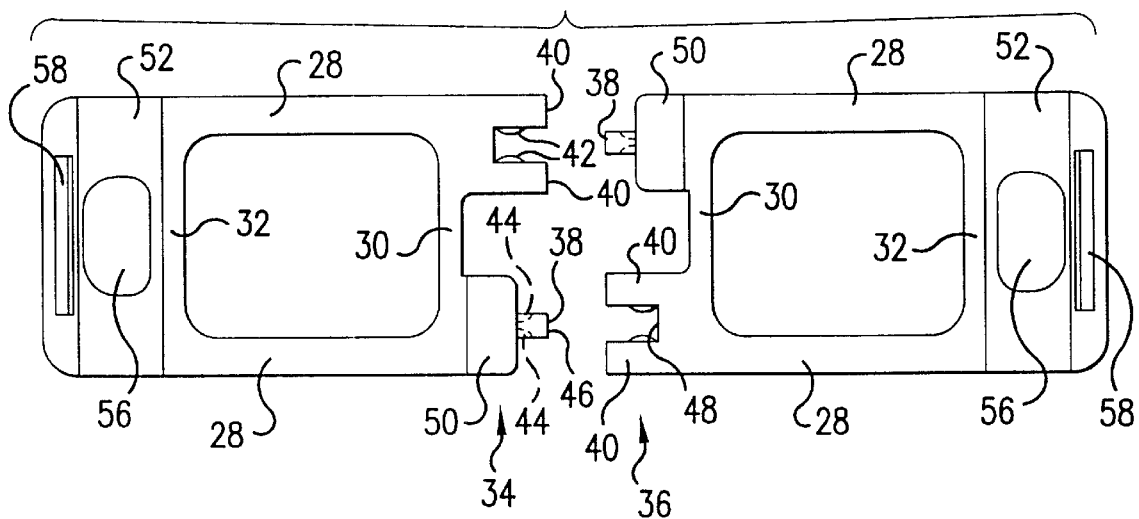
FIG. 4 is an exploded plan view of a pair of articulator arms of the present invention.
Figure 5:
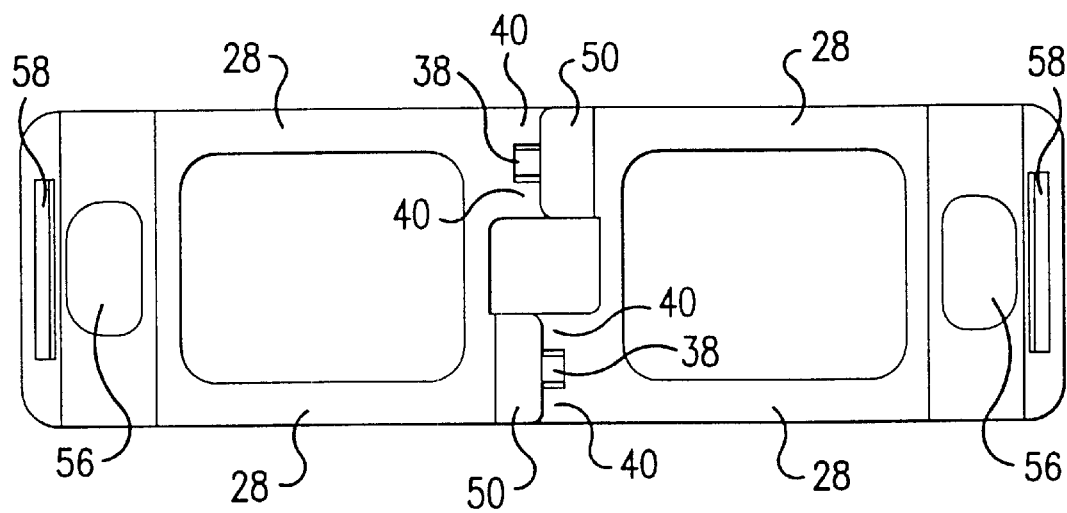
FIG. 5 is a plan view of the pair of articulator arms attached together.
Figure 6:
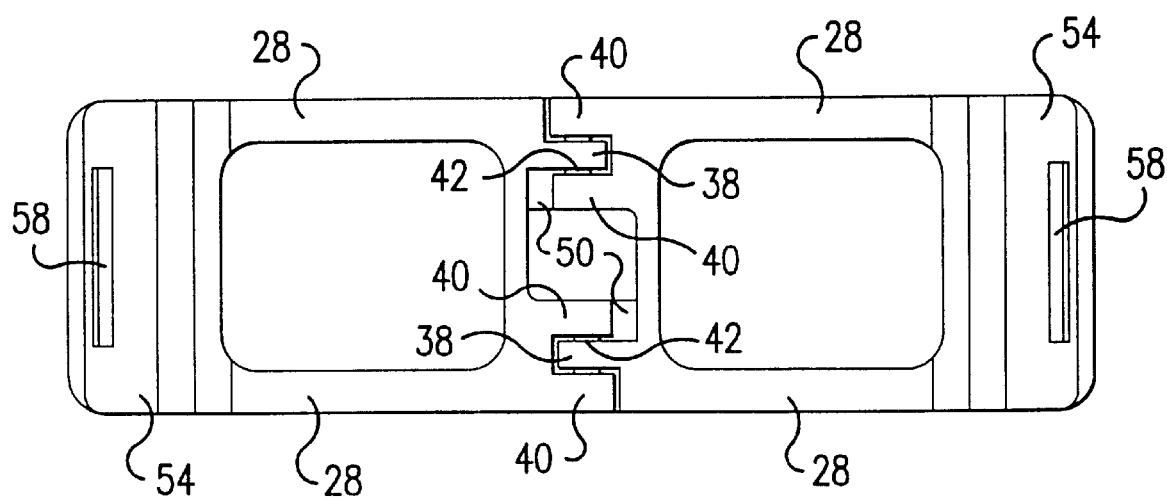
FIG. 6 is a bottom view of the pair of articulator arms in an assembled condition.

The cross-member 30 of the first articulator 22 supports a first hinge portion 34. Accordingly, the second articulator arm 24 supports a second hinge portion 36 which may be matingly engaged with the first hinge portion 34 to form the hinge 26. The first hinge portion 34 includes a first finger 38 extending from the cross-member 30 near one end thereof. A pair of second fingers 40 extend from the first cross-member 30 adjacent the other end thereof. As can be seen in FIGS. 4 and 6, the first fingers 38 of one articulator arm are insertable between the second fingers 40 of the other articulator arm.

Each of the second fingers 40 includes a projection 42 extending therefrom in a direction toward the opposing second finger 40. Each of the first fingers 38 include a pair of dimples 44, with one dimple 44 being formed on each side of the first finger 38. The dimples 44 are shaped to correspond with the profile of the projections 42. When the first articulator arm 22 is assembled with the second articulator arm, the projections 42 of the second fingers 40 of the first articulator arm 22 are located within the dimples 44 of the first finger 38 of the second articulator arm 24. Similarly, the projections 42 of the second fingers 40 of the second articulator arm 24 are located in the dimples 44 of the first finger 38 of the first articulator arm 22. The first articulator arm is pivotable with respect to the second articulator arm 24 about a pivot axis defined by a line drawn through the centers of the aligned projections 42 and dimples 44.

Each of the first fingers 38 includes an introduction area 45 surrounding the dimples 44. Thus, when the first articulator arm 22 is partially assembled with the second articulator arm 24, the projections 42 may slide along the introduction area 45 surrounding the dimples 44. Thus, although the projections 42 may not be properly seated in the dimples 44, the projections 42, and thus the second fingers 20, are nonetheless held in position by the frictional forces between the projections 42 and the introduction area 45. Also, as the first articulator arm is being assembled with the second articulator arm 24, and the first finger 38 is being inserted between the second fingers 40, a gap between the second fingers 40 increases slightly to allow the first finger 38 to slide past the projections 42 until the projections 42 are properly seated in the dimples 44, at which time the second fingers move back to their original position because of the elasticity of the material from which the articulator arms are formed. Preferably, the material forming the articulator arms is a thermoplastic material, although other suitable materials may be utilized.

When the dental modeling system 10 is formed as shown in FIG. 1, the hinge 26 permits movement of the upper support 12 with respect to the lower support 14 to simulate the three movements of the human jaw, those being centric, protrusive and excursion, by appropriately pivoting the hinge about the interconnection between the projections 42 and the dimples 44, or by shifting the projections 42 out of the dimples 44 and moving them along the introduction areas 45.

The first cross-member 30 is generally parallel with the second cross-member 32, and both the first and second cross members 30, 32 extend generally perpendicular to the pair of arms 28.

Figure 3:
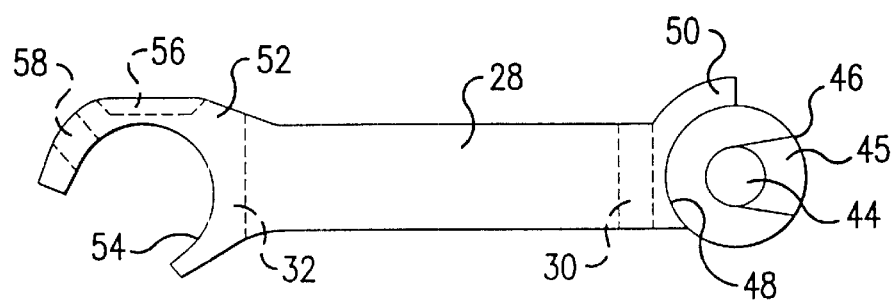
FIG. 3 is a side view of an articulator arm of the present invention.

As shown in FIG. 3, end portions 46 of each of the first and second fingers 38, 40 have a circular profile which is received in a correspondingly shaped recess 48. As the first articulator arm 22 pivots with respect to the second articulator arm 24 about the hinge 26, the end portions 46 of the fingers slide along the recesses 48, thereby providing a well-defined movement with high strength. However, it should be understood that the articulator arms 22, 24 may be configured such that sliding does not occur between the end portions 46 and the recesses 48, but rather a clearance is provided therebetween. To increase the area of the recesses 48, a wing 50 is provided which extends outwardly from the first cross-member 30, as shown in FIGS. 3 and 4. This provides a resistance to compression forces between mounted maxillary and mandibular casts, especially when there are multiple missing teeth.

The second cross-member 32 supports a socket member 52 which receives and supports an appropriately shaped attachment member of a support, such as the upper support 12. The interior surface of the socket member 52 is formed as an elongated part-cylindrical surface 54. The outer surface of the socket member 52 includes a depression 56 therein for receiving a finger or thumb of a user. In addition, a glue slot 58 is provided in the socket member 52 which penetrates from the outer surface to the elongated part-cylindrical surface 54. The part-cylindrical surface 54 of the socket member 52 is formed as an arch as shown in FIG. 3 which traverses more than 180° so that a cylindrical or spherical element placed into the socket member 52 will be retained thereby. The articulator arm 22 is formed of a thermoplastic material, and thus the opening of the socket member 52 may increase slightly as an attachment member is inserted thereinto, and may return to its original shape shown in FIG. 3 to thereby retain the attachment member in the socket member 52.

Figure 2:
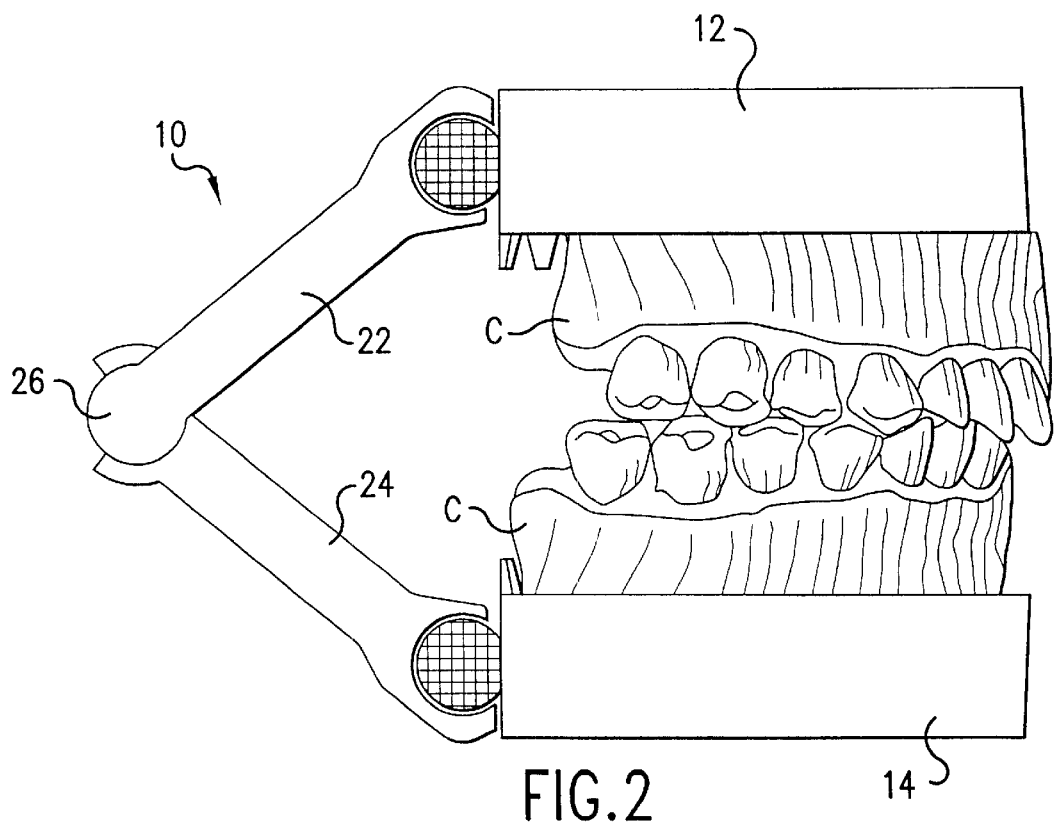
FIG. 2 is a side view of the dental articulator shown in FIG. 1, and having dental casts attached thereto.

When the first articulator arm 22 is assembled with the second articulator arm 24, the articulator arms 22, 24 are pivotable about the hinge 26 until a point is reached wherein portions of the articulators arms 22, 24 adjacent to the first cross-members 30 engage one another, thereby preventing further closing movement of the articulator arms. Such a stop position is shown in FIG. 2, for example.

The lower support 14 will now be described in detail with particular reference to FIGS. 7–11. The upper surface 18 of the lower support 14 includes a plurality of registration pins 70 extending upwardly from the upper surface 18. The registration pins 70 are evenly spaced apart and aligned in a row extending centrally along the upper surface 18 of the main body 16. However, the lower support 14 may be configured such that the registration pins 70 are unevenly spaced apart, or may be arranged in more than one row, such as two rows, or a row not extending along the center of the main body 16. The registration pins 70 are tapered inwardly in a direction proceeding away from the upper surface 18. Preferably, the registration pins 70 are formed as pyramidal elements with the top portion thereof removed to form truncated pyramids, and each of the sides of the registration pins 70 is a flat, planar side. In each of the embodiments disclosed herein, the registration pins 70 are formed integrally with the main body 16 as a one-piece unit. However, it is envisioned that the registration pins 70 may be formed on a separate subbody which is received and supported on the main body 16.

In the embodiment disclosed, a first pair of the sides of the registration pins 70 taper inwardly at a first angle, and a second opposing pair of the sides of the registration pins 70 taper inwardly at a second angle different from the first angle. The registration pins 70 preferably have a rectangular base with a length dimension extending along a longitudinal axis of the main body, and a width dimension extending transversely to the longitudinal axis. The length dimension is preferably greater than the width dimension. In one embodiment, the registration pins 70 have a height dimension which is greater than the length dimension and the width dimension. Preferably, adjacent ones of the registration pins 70 are spaced-apart from one another by a distance less than the length dimension of the base of the registration pins 70.

Located on each side of the registration pins 70 are two rows of holes 72. The holes 72 are also evenly spaced and arranged in rows extending parallel to the row of registration pins 70. However, other arrangements of the holes 72 may be made other than the two parallel rows of evenly spaced holes 72, as set forth herein. The holes 72 are circular in cross-section and taper inwardly extending into the main body 16 from the upper surface 18.

Located outwardly of the holes 72 are a first groove 74 and a second groove 76. The first groove 74 is formed by a pair of straight first groove portions 74a extending parallel to the rows of holes 72 and registration pins 70. One end of each of the straight first groove portions 74a terminates at the rear wall 78 of the main body 16, and the other ends of the straight first groove portions 74a are interconnected by a semi-circular curved first groove portion 74b. Similarly, the second groove 76 is formed by a pair of straight second groove portions 76a extending parallel to the straight first groove portion 74a and outwardly thereof. One end of the straight second groove portion 76a terminates at the rear wall 78, and the other ends of the straight second groove portions 76a are interconnected by a semi-circular curved second groove portion 76b. Except for the presence of the registration pins 70 extending upwardly from the upper surface 18, and the presence of the first and second grooves 74, 76 extending into the main body 16, the upper surface 18 is essentially flat and forms a stable planar base for receiving casting stone material thereon for forming a dental cast C.

Figure 7:
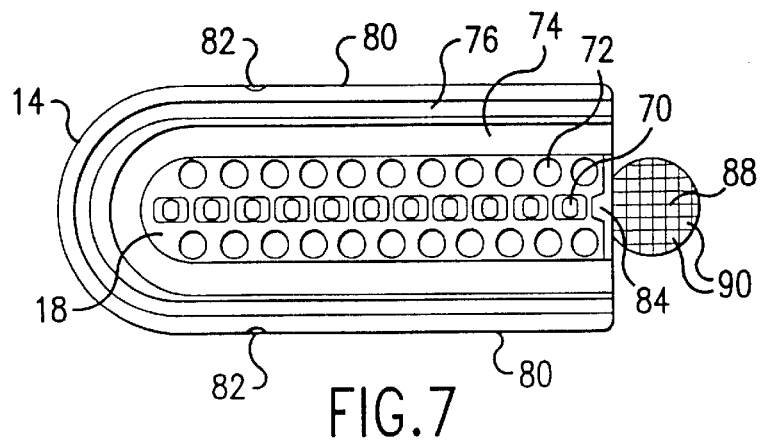
FIG. 7 is a top view of a support for a dental cast according to a first embodiment of the invention.
Figure 8:
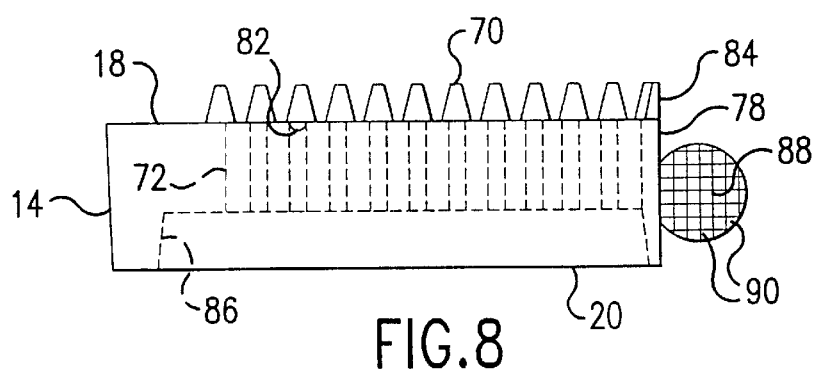
FIG. 8 is a side view of the support shown in FIG. 7.

As shown in FIG. 7, the first groove 74 is wider and deeper than the second groove 76, although equally sized grooves may be utilized. Although the grooves 74, 76 are continuous from one end to another, the grooves may also be configured as segmented discontinuous groove segments.

Extending between the upper surface 18 and the lower surface 20 are side walls 80. As evident from FIGS. 10 and 11, the side walls are tapered slightly inwardly from the upper surface 18 to the lower surface 20. This tapering of the side walls 80 permits the removal of excess stone material from the dental cast C by utilizing a grinding wheel without causing damage to the entire side wall 18 of the lower support 14. Instead, the excess stone may be ground away until only the uppermost portion of the side wall 80 engages the grinding wheel.

A pair of notches 82 are located in the upper portion of the side walls 80 adjacent the upper surface 18, which are utilized to identify the approximate location of the cuspids of the dental cast C. Also, the notches 82 provide a convenient entry point for a tool, such as a screwdriver, which may be inserted into the notch to pry the dental cast C off of the upper surface 18 of the lower support 14. Further, to ease the separation of the dental cast C from the lower support 14, the upper surface 18 may be coated with silicone or an oil based spray which acts as a separating medium for removing the dental cast C from the upper surface 18 of the lower support 14.

In order to prevent the unhardened casting stone from sliding off of the upper surface 18 and onto the rear wall 78, a blocking member 84 is provided which extends upwardly from the upper surface 18 adjacent the rearmost registration pin 70.

Figure 9:
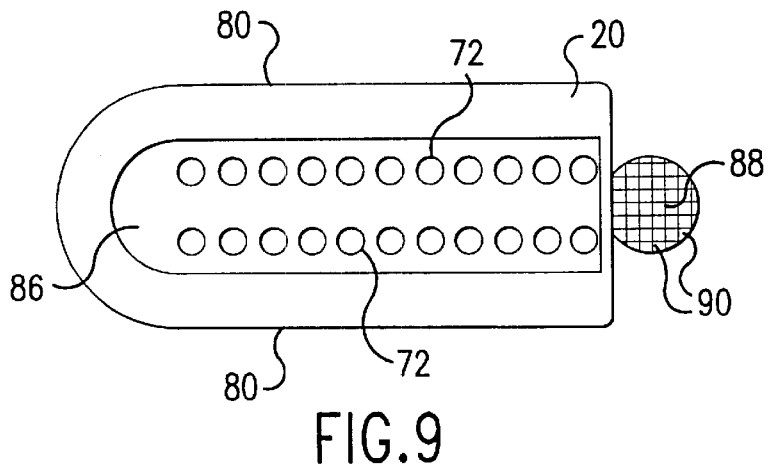
FIG. 9 is a bottom view of the support shown in FIG. 7.
Figure 10:
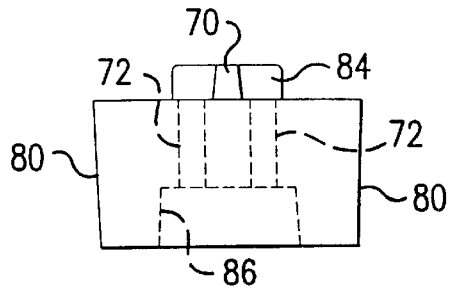
FIG. 10 is a front end view of the support shown in FIG. 7.
Figure 11:
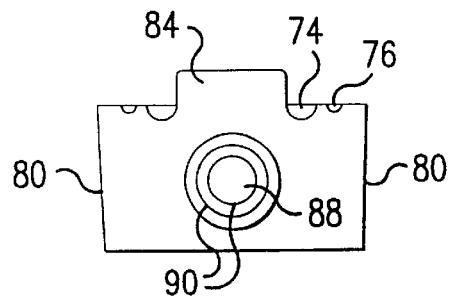
FIG. 11 is a rear end view of the support shown in FIG. 7.

The lower surface 20 of the main body 16 includes a cavity 86 therein. The holes 72 extend through the main body 16 and terminate with openings in the cavity 86 as shown in FIG. 9. The rear wall 78 of the main body 16 includes an attachment ball 88 thereon. The attachment ball 88 is formed of a part spherical member connected to the rear wall 78. The attachment ball 88 includes a plurality of grooves 90 extending into the surface of the attachment ball 88. The grooves extend either partially or fully circumferentially around each attachment ball, and the grooves 90 may intersect with one another. The attachment ball 88 and the elongated part-cylindrical surface 54 of the socket member 52 form a joint which provides four degrees of freedom of movement of the support 12, 14 with respect to the articulator arm 22, 24. The four degrees of freedom include three degrees of rotation of the attachment ball 88 about mutually orthogonal axes, and one degree of translation of the attachment ball 88 along the axis of the elongated part-cylindrical surface 54 of the socket member 52.

When the attachment ball 88 is inserted into the elongated part-cylindrical surface 54 of the socket member 52 as shown in FIG. 2, glue is applied to the junction between the attachment ball 88 and the cylindrical surface 54. The glue slot 58 and the socket member 52 permits the glue to be inserted more readily into the interior junction between the attachment ball 88 and the cylindrical surface 54. Further, the depression 56 permits a user applying the glue to firmly hold the articulator arm 22 without the glue contacting the users finger. The grooves 90 in the attachment ball 88 permit the glue to flow along the attachment ball by capillary action or wicking action, thereby promoting the flow of adhesive along the entire junction, thereby resulting in a superior bond.

As used herein, the plurality of grooves formed in a surface which permits the flow of adhesive thereinto and therealong is termed "glue mesh".

Figure 12:
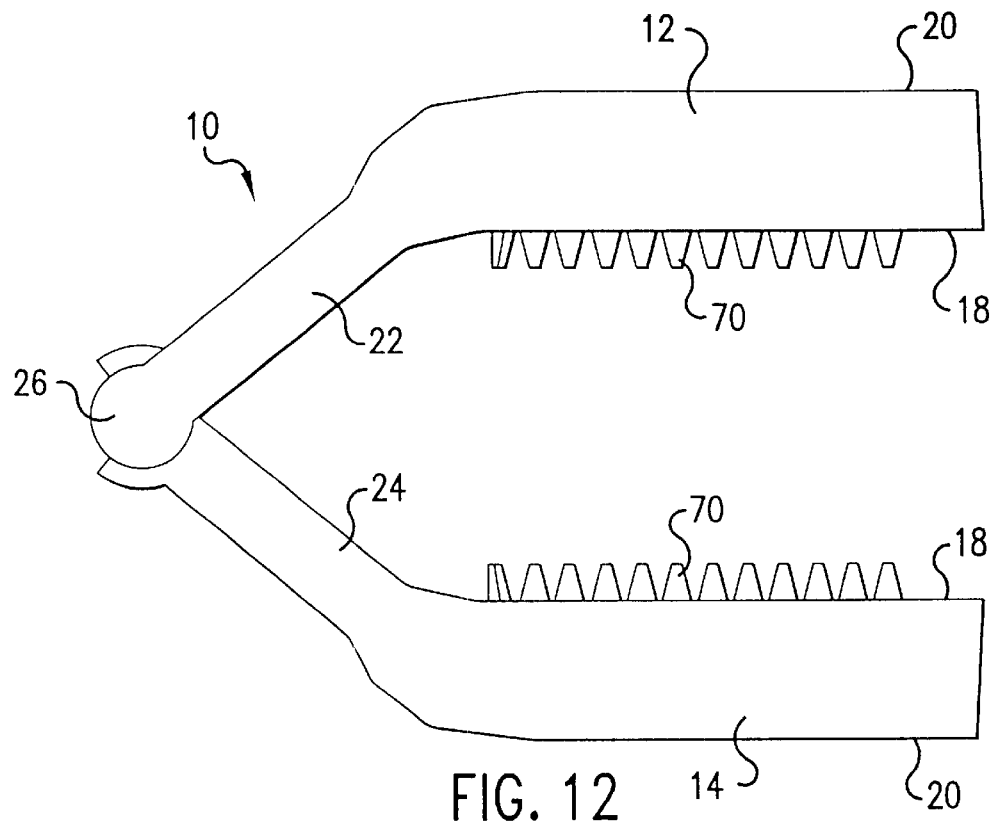
FIG. 12 is a dental articulator according to a second embodiment of the present invention.
Figure 13:
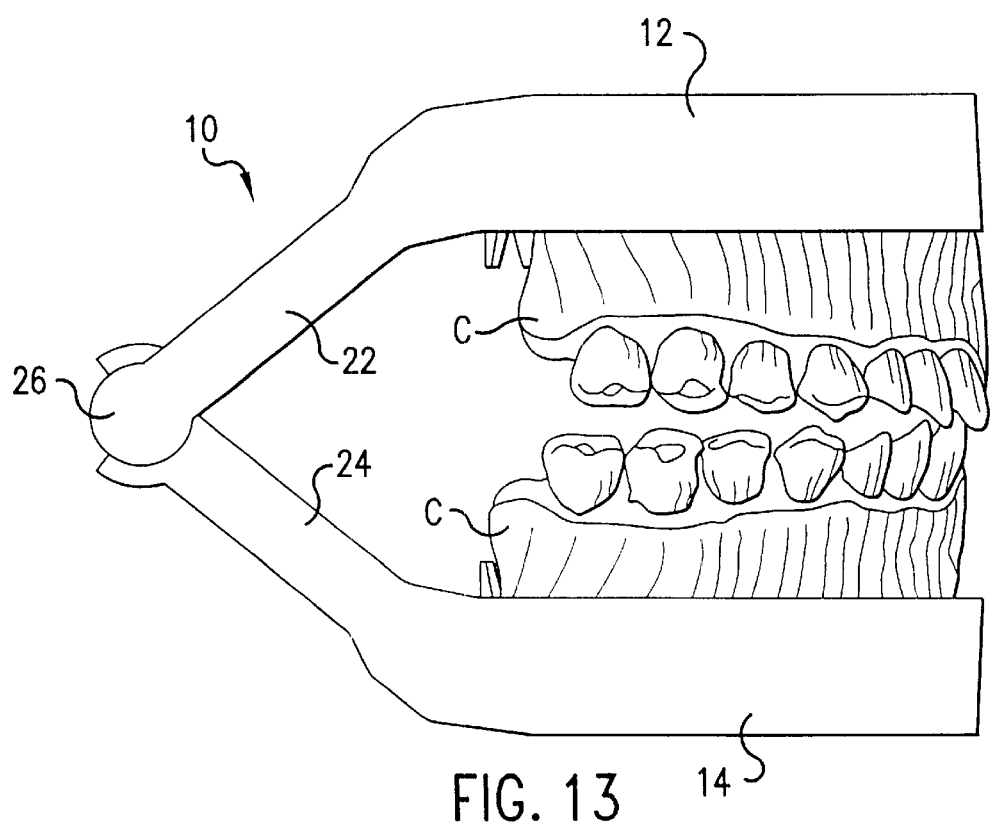
FIG. 13 is a side view of the dental articulator shown in FIG. 12 with dental casts attached thereto.
Figure 14:
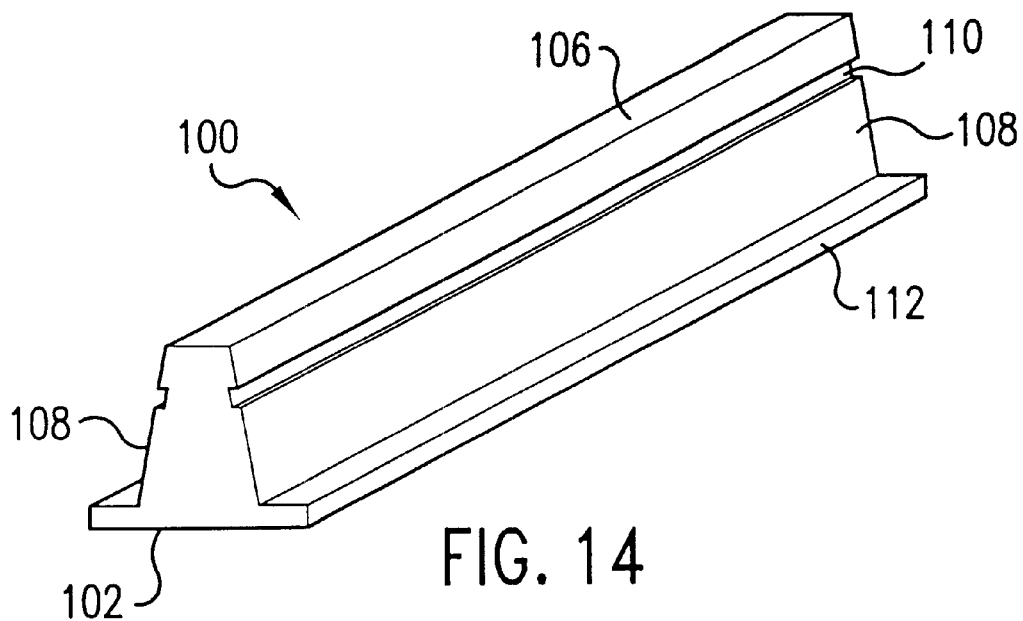
FIG. 14 is a perspective view of an auxiliary support member, or auxiliary cap, of the present invention.
Figure 15:
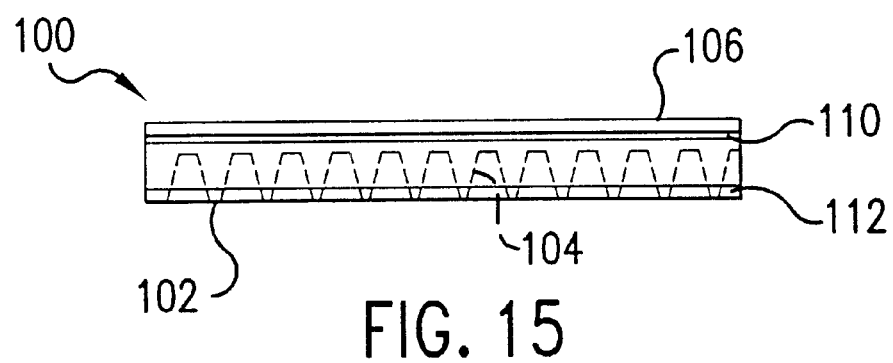
FIG. 15 is a side view of the auxiliary cap of the present invention.
Figure 16:
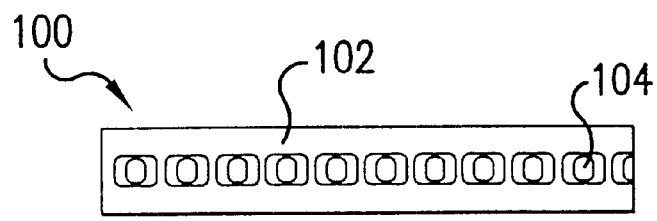
FIG. 16 is a bottom plan view of the auxiliary cap of the present invention.

As shown in FIGS. 1 and 2, the upper and lower supports 12, 14 are attached to the first and second articulator arms 22, 24, respectively, utilizing the ball and socket arrangement which is held in position with glue, such as a fast acting cryanoacrylic glue. However, as shown in FIGS. 12 and 13, the upper and lower supports 12, 14 may be formed directly with the first and second articulator arms 22, 24, respectively, with each being a one-piece unitary member. This eliminates the necessity for the attachment ball 88 and the socket member 52, and thus eliminates the requirement for gluing.

In practice, casting stone may be placed on the upper surface 18 of the main body 16, and the negative impression of the patient's teeth taken the by the dentist may be pressed onto the casting stone. The main body 16 and the negative impression may be pressed toward one another so that the casting material flows into the negative impression and into the first and second grooves 74, 76 of the main body 16. At that time, a portion of the casting material will flow into the holes 72 which, when the casting material is removed from the upper surface 18, provides additional registration points between the dental cast C and the main body 16. The provision of the registration pins 70 provides sufficient registration of the dental cast C with respect to the main body 16, even if the dental cast is segmented into smaller portions comprising one or two teeth registered by just one registration pin 70. The holes 72 provide an additional mechanism whereby a dental technician may insert one or more pins P thereinto prior to placing the casting material onto the upper surface 18. Thus, when the dental cast C is separated from the main body 16, the pins are fixed to the dental cast C and can be reinserted into the holes 72 to provide additional registration elements between a dental cast C and the main body 16. Although the holes 72 are tapered, it should be understood that cylindrical holes may be utilized as well. However, the tapered holes 72 permit the use of a tapered pin which provides a very positive connection between the pin and the corresponding hole 72.

When a dental cast C is formed on the upper surface 18, it is possible to assist the separation of the dental cast C from the upper surface 18 by blowing air into the cavity 86 and through the holes 72. Alternatively the main body 16 may be pressed down onto an ejector block (not shown) having a plurality of ejector pins extending upwardly therefrom which pass through the holes 72 and against the bottom surface of the dental cast C. Further, as set forth above, a tool may be inserted between dental cast C and the upper surface 18, for example at the notch 82, to promote separation of the dental cast from the upper surface 18.

As shown in FIGS. 14–18, an auxiliary cap 100 may be utilized with the upper support 12 and/or the lower support 14. The auxiliary cap 100 is configured with a lower surface 102 which engages with the upper surface 18 of the main body 16. The lower surface 102 therefore includes a plurality of recesses 104 which are correspondingly shaped to receive the registration pins 70 of the main body 16. These recesses 104 cooperate with the registration pins 70 to provide a unique registration of the auxiliary cap 100 with respect to the main body 16.

The auxiliary cap 100 has an upper surface 106 and a pair of opposing tapered sidewalls 108. The sidewalls 108 of the auxiliary cap 100 are tapered in the manner of the registration pins 70 of the main body 16. The sidewalls 108 include a pair of longitudinal grooves 110 therein. The grooves 110 act as interlocking mechanisms which promote the adhesion of the dental cast C thereonto which allows the casting material to flow thereinto and become essentially locked in place. A flange 112 is located at the bottom of the auxiliary cap 100 for engaging the upper surface 18 of the main body 16. In use, the casting stone is placed on the upper surface 106 of the auxiliary cap 100 instead of on the upper surface 18 of the main body 16. The dental cast C thereby formed is thus permanently affixed to the auxiliary cap 100 which may be removed from and reinserted onto the main body 16. Additionally, the auxiliary cap 100 may be cut into segments along with the dental cast C, and these segments are reliably repositionable onto the upper surface 18 of the main body 16 in proper registration with the remaining dental cast C.

Figure 17:
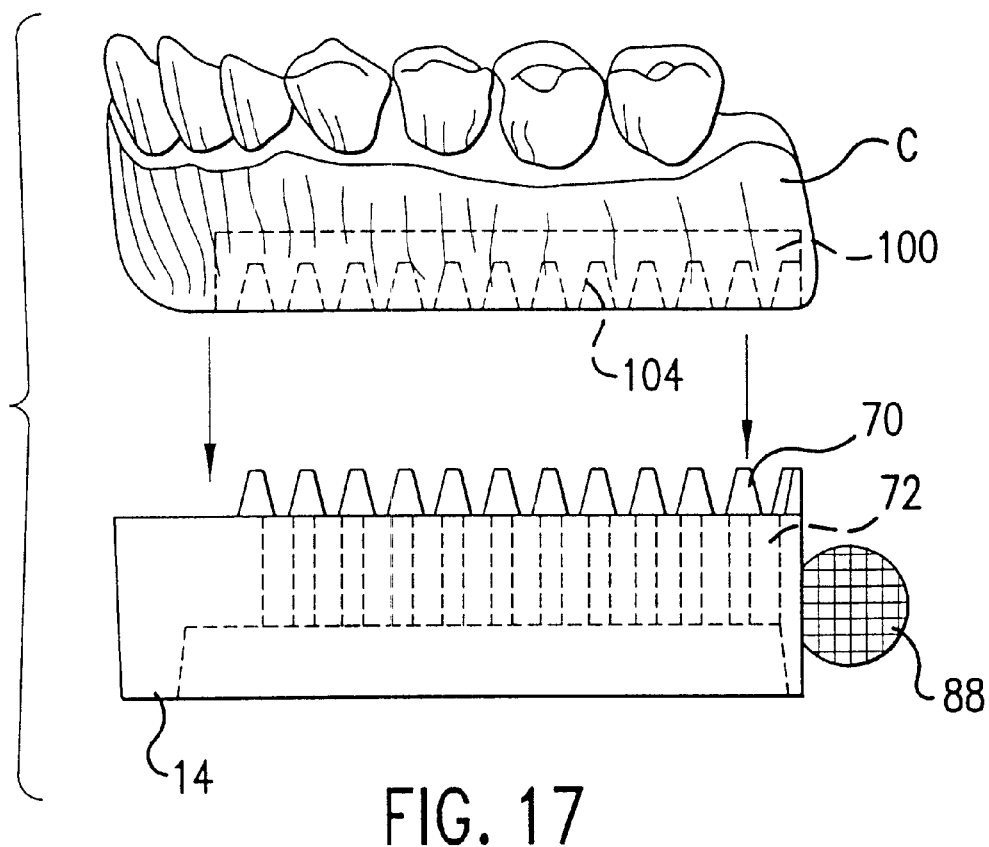
FIG. 17 is an exploded side view showing the auxiliary cap with a dental casting thereon being attached to the support member of the first embodiment.
Figure 18:
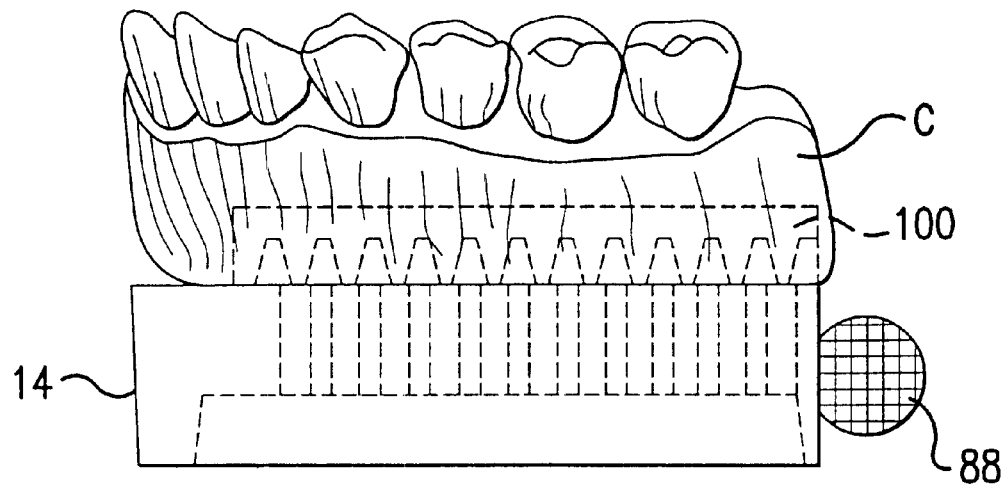
FIG. 18 is a side view showing the auxiliary cap attached to the support member of the first embodiment.

As shown in FIG. 17, the auxiliary cap 100 with the dental cast C formed thereon is locatable above the upper surface 18 of the main body, and is lowered thereon to a position shown in FIG. 18 wherein the registration pins 70 of the main body 16 are located within the recesses 104 of the auxiliary cap 100 to firmly and accurately retain the auxiliary cap 100 onto the main body 16 in a proper registrational relationship.

Figure 19:
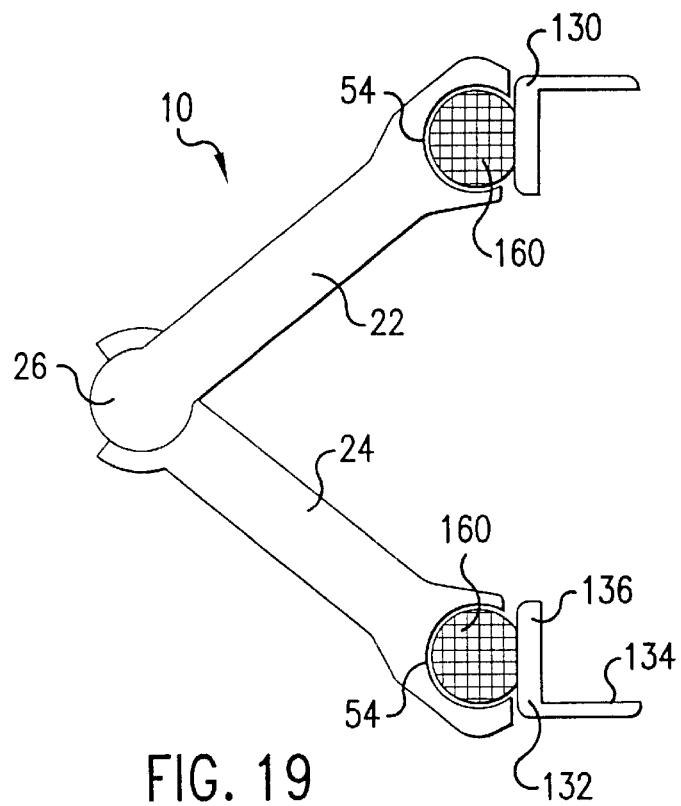
FIG. 19 is a side view of a dental articulator according to a third embodiment of the present invention utilizing a support according to a second embodiment.
Figure 20:
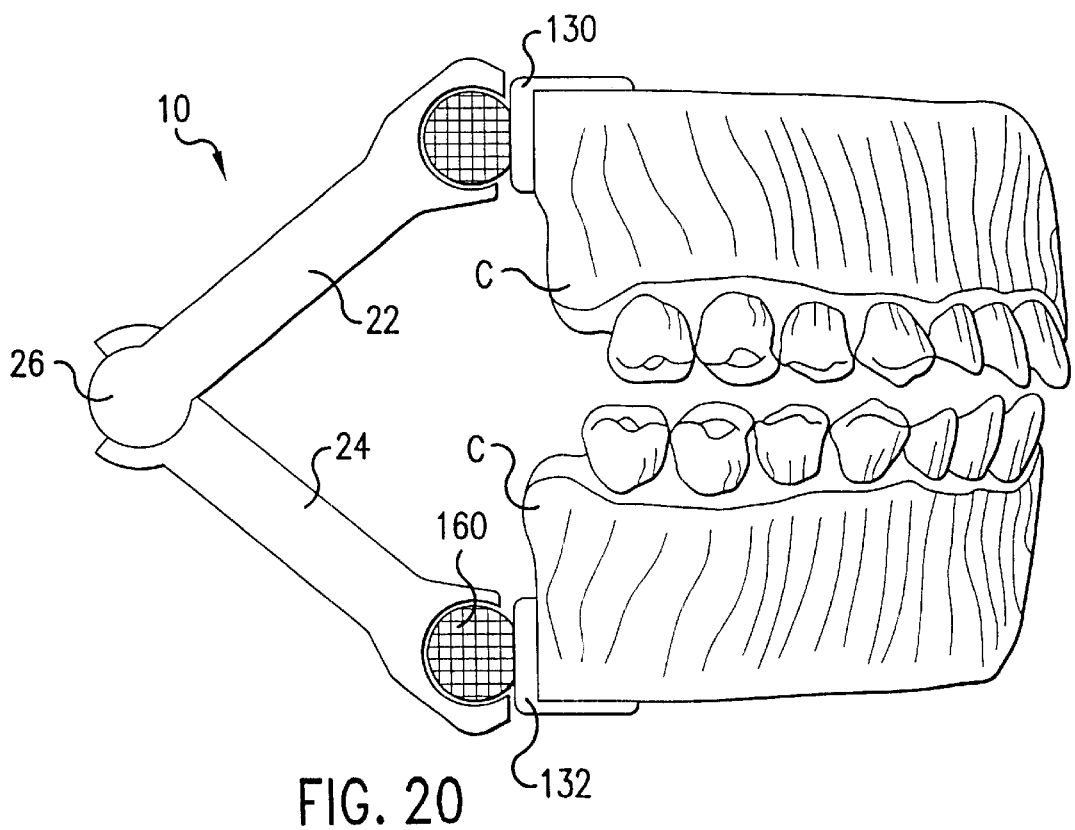
FIG. 20 is a side view of the dental articulator shown in FIG. 19 with dental casts attached thereto.
Figure 21:
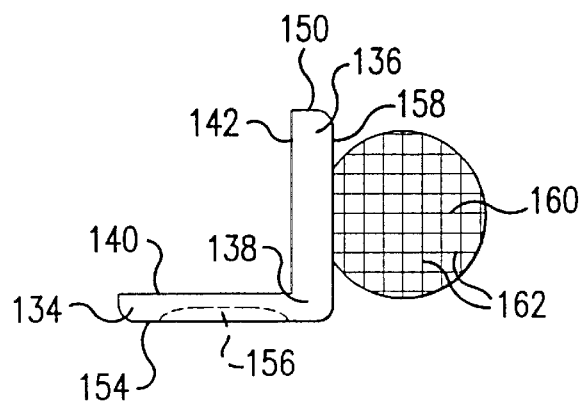
FIG. 21 is a side view of the support shown in FIG. 19.
Figure 22:
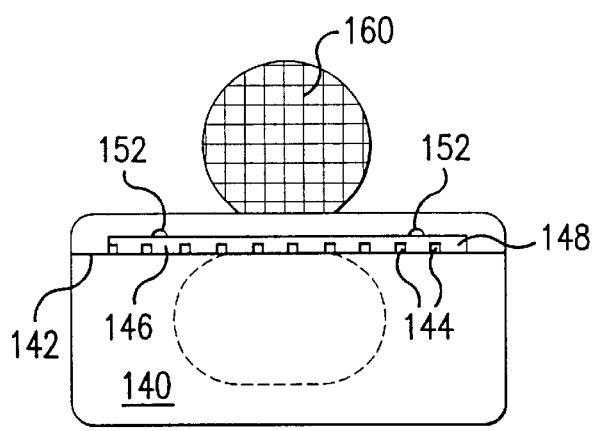
FIG. 22 is a top view of the support shown in FIG. 21.
Figure 23:
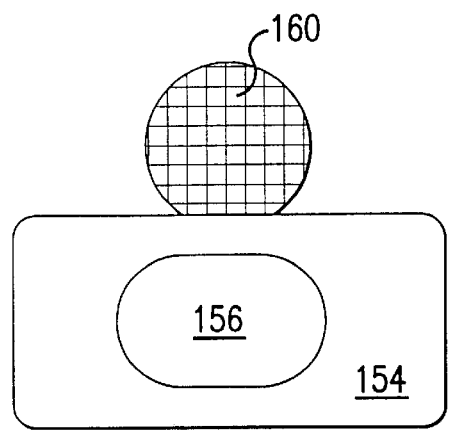
FIG. 23 is a bottom view of the support shown in FIG. 21.
Figure 24:
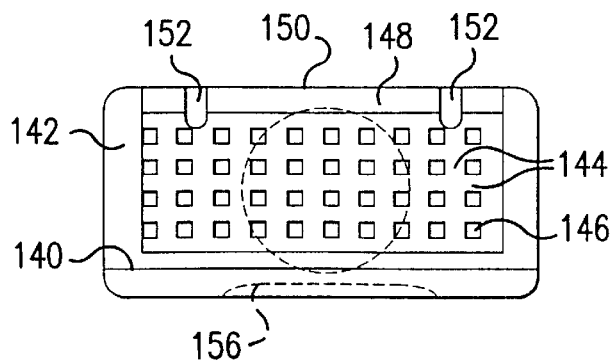
FIG. 24 is a front end view of the support shown in FIG. 21.
Figure 25:
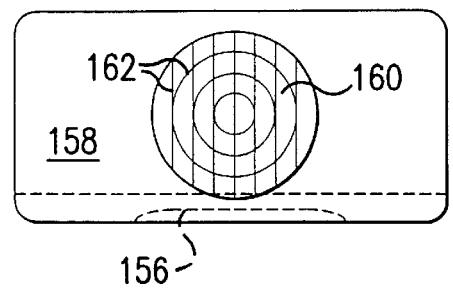
FIG. 25 is a rear end view of the support shown in FIG. 21.

Referring now to FIGS. 19–25, a third embodiment of the dental modeling system will now be described in detail. As shown in FIG. 19, a first articulator arm 22 is pivotally attached to a second articulator arm 24. The articulator arms 22, 24 are the same as those shown in the embodiment of FIG. 1. However, the upper support 12 and the lower support 14 of the FIG. 1 embodiment have been replaced by an upper support 130 and a lower support 132 in the FIG. 19 embodiment. The upper support 130 is identical to the lower support 132, and a discussion will be made with respect to the lower support 132 with the understanding that the same discussion applies to the upper support 130. The lower support 132 includes a bottom member 134 and a back member 136 which together form an L-shaped main body 138.

The bottom member has an inner surface 140, and the back member 136 has an inner surface 142 which together receive a dental cast C thereon. The inner surface 140 and the inner surface 142 are oriented at approximately 90° with respect to one another. This allows a dental cast C which typically contains a bottom wall and rear wall which meet at a 90° angle to be properly secured to the main body 138.

The inner surface 142 of the back member 136 includes a glue mesh arrangement formed by a plurality of intersecting grooves 144 which extend into the inner surface 142, thus forming a plurality of raised projections 146 between adjacent intersecting grooves 144. A glue slot 148 is located at the intersection of the inner surface 142 and a top wall 150 of the back member 136. Also, a plurality of glue holes 152 are arranged along the top wall 150 which communicate with the glue slot 148.

To secure the dental cast C to the main body 138, the base of the dental cast C is placed against the bottom member 134 and the back member 136. Glue may then be applied into the glue holes 152 and the glue slot 148, which then passes into the intersecting grooves 144 by capillary or wicking action, which thereby provides a large surface area of glue contact between the back member 136 and the dental cast C.

The inside surface 140 of the bottom member 134 is generally flat. However, it is envisioned that the inside surface 140 may also include a glue mesh arrangement as does the inner surface 142 of the back member.

The bottom member 134 includes an outer surface 154 which includes a depression 156 therein. The depression 156 is similar to the depression 56 of the articulator arms 22, 24. The depression 156 provides a convenient resting point for the finger or thumb of a technician applying glue to the interface between the dental cast C and the main body 138.

The back member 136 includes an outer surface 158 which includes an attachment ball 160 thereon. The attachment ball 160 is similar to the attachment ball 88 shown in FIG. 7. The attachment ball 160 includes a plurality of grooves 162 which are similar to the grooves 90 in the attachment ball 88. The discussion set forth previously with respect to the attachment ball 88 and the grooves 90 is equally applicable to the attachment ball 160 and the grooves 162 of the lower support 132. The grooves 162 form a glue mesh arrangement as described previously.

The lower support 132 is attached to the second articulator arm 24 by gluing the attachment ball 160 to the socket member 54 in the manner described above with respect to the lower support 14. Further, although not shown in the drawings, it should be understood that the lower support 132 and/or the upper support 130 may be formed as an extension of the articulator arms 24, 22 respectively, in the same manner as that shown in the embodiment of FIGS. 12 and 13. Further, it may be desirable to configure the articulator arms 22, 24 with an upper support 12 and a lower support 132. This may occur, for example, when the dental technician already has a lower dental cast C formed, but needs only to pour and form a mating upper dental cast C utilizing the upper support 12.

Figure 26:
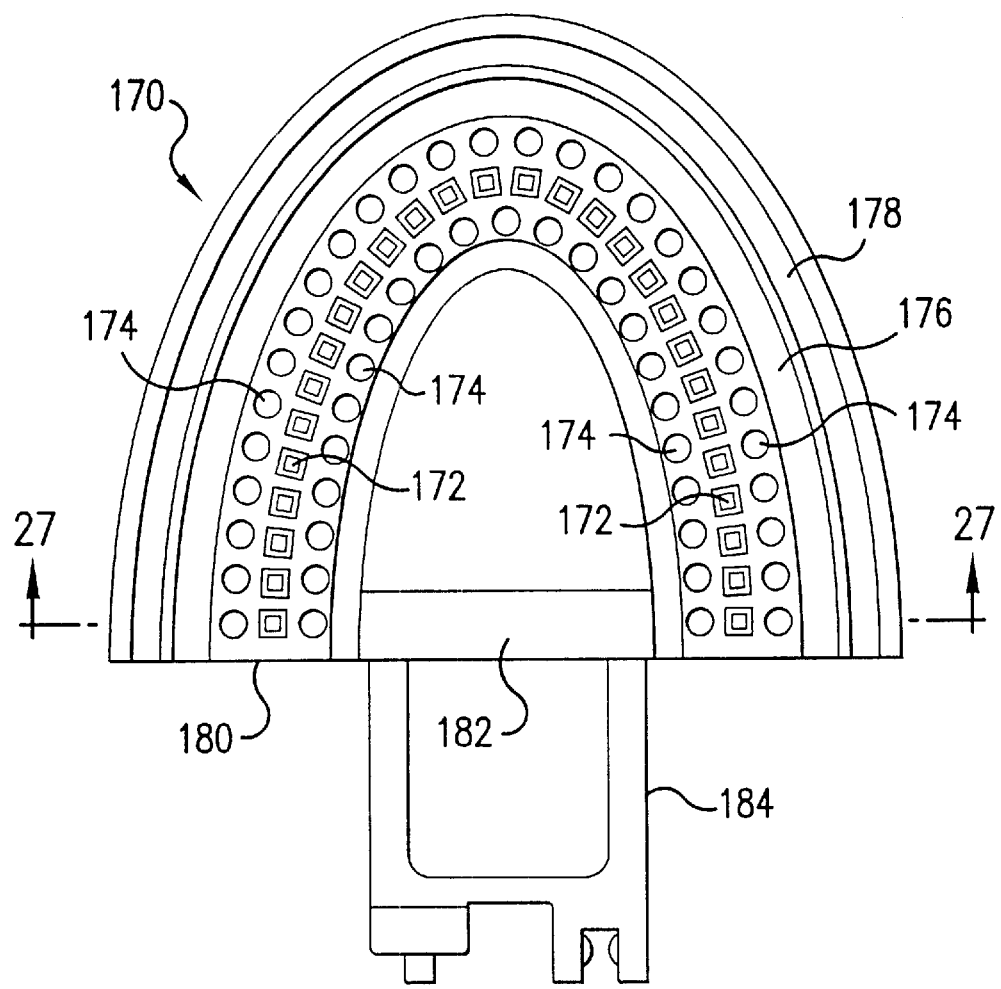
FIG. 26 is a plan view of a full-arch support of the present invention.
Figure 27:
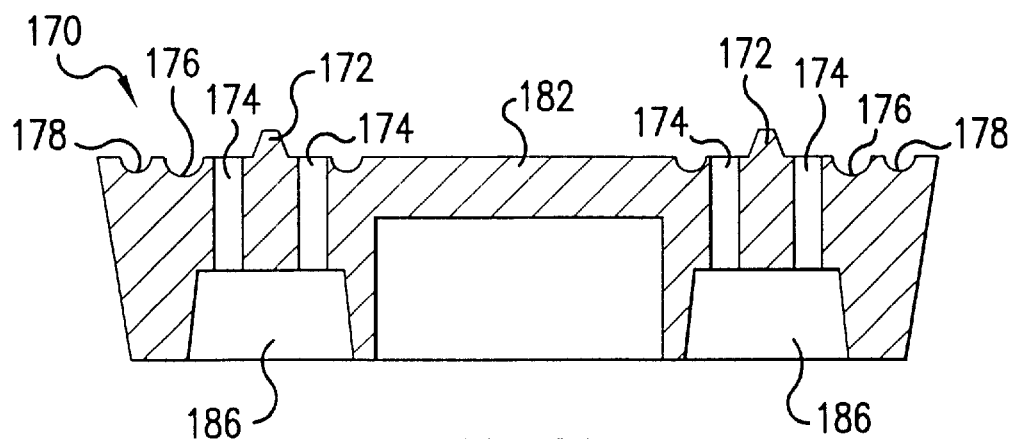
FIG. 27 is a cross-sectional view taken along lines 27—27, in FIG. 26.

Referring now to FIGS. 26 and 27, a full arch support 170 is shown. The full arch support 170 includes a row of registration pins 172, two rows of holes 174, a first groove 176 and a second groove 178 which essentially correspond to the registration pins 70, the holes 72, the first groove 74 and the second groove 76 described above with respect to FIG. 7. The full arch support 170 has a rear wall 180 including a cross-member 182 attached thereto. The cross-member 182 provides an attachment point for an articulator arm 184. The articulator arm 184 is essentially the same as the articulator arm 22, except that no socket member is required since the articulator arm 184 is directly attached to the cross-member 182. However, it should be understood that an articulator arm identical to the second articulator arm 24 may be utilized with the full arch support 170, provided that a compatible attachment ball is provided on the cross-member 182 which would then be glued in place in the manner described previously. The full arch support 170 includes a cavity 186, as shown in FIG. 27. Although not shown in the drawings, an auxiliary base member such as that shown in FIG. 14 may be utilized with the full arch support 170 shown in FIG. 26, provided that it is shaped in the full arch manner.

In the embodiments shown in FIGS. 28–39, certain modifications of the previously described embodiments have been made. The modifications and differences will be described in detail. However, the description of the similarities has been omitted for brevity.

Figure 28:
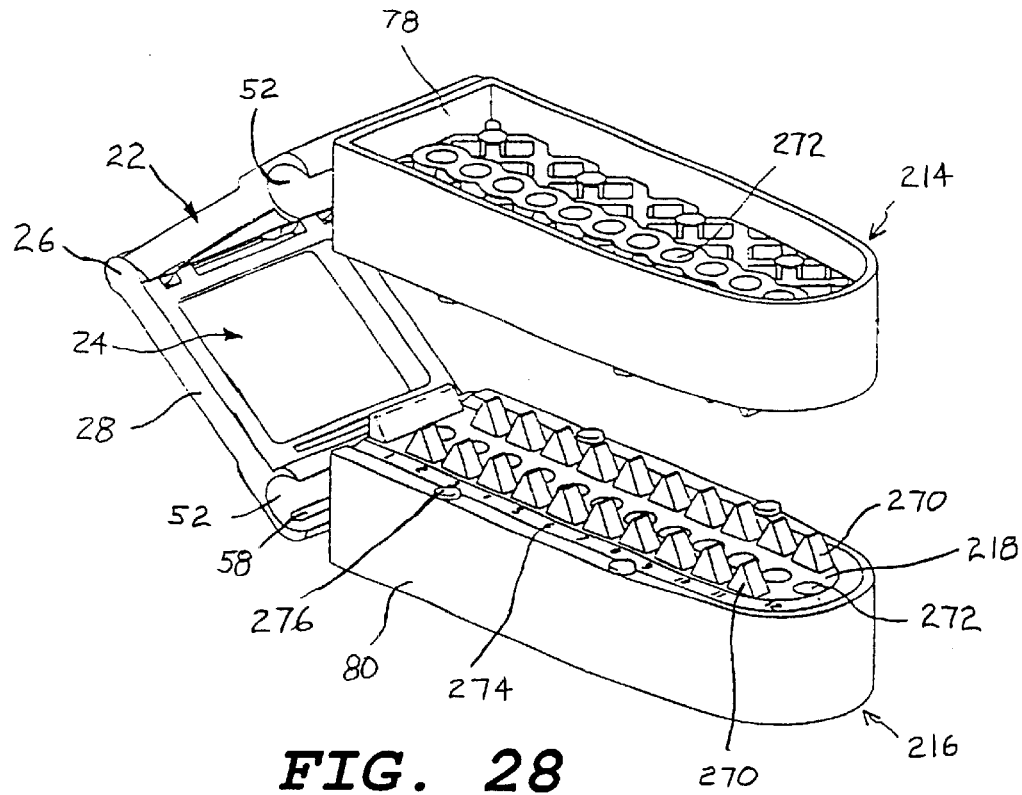
FIG. 28 is a perspective view of a modified form of the dental articulator shown in FIG. 1.
Figure 29:
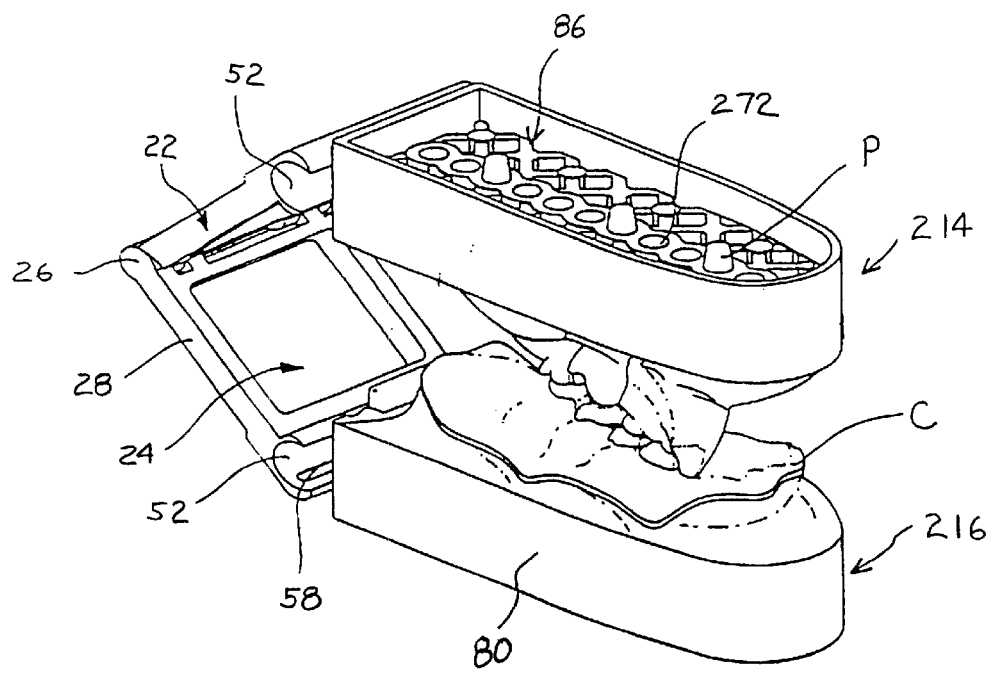
FIG. 29 is a perspective view of the dental articulator shown in FIG. 28 with dental casts attached thereto.
Figure 30:
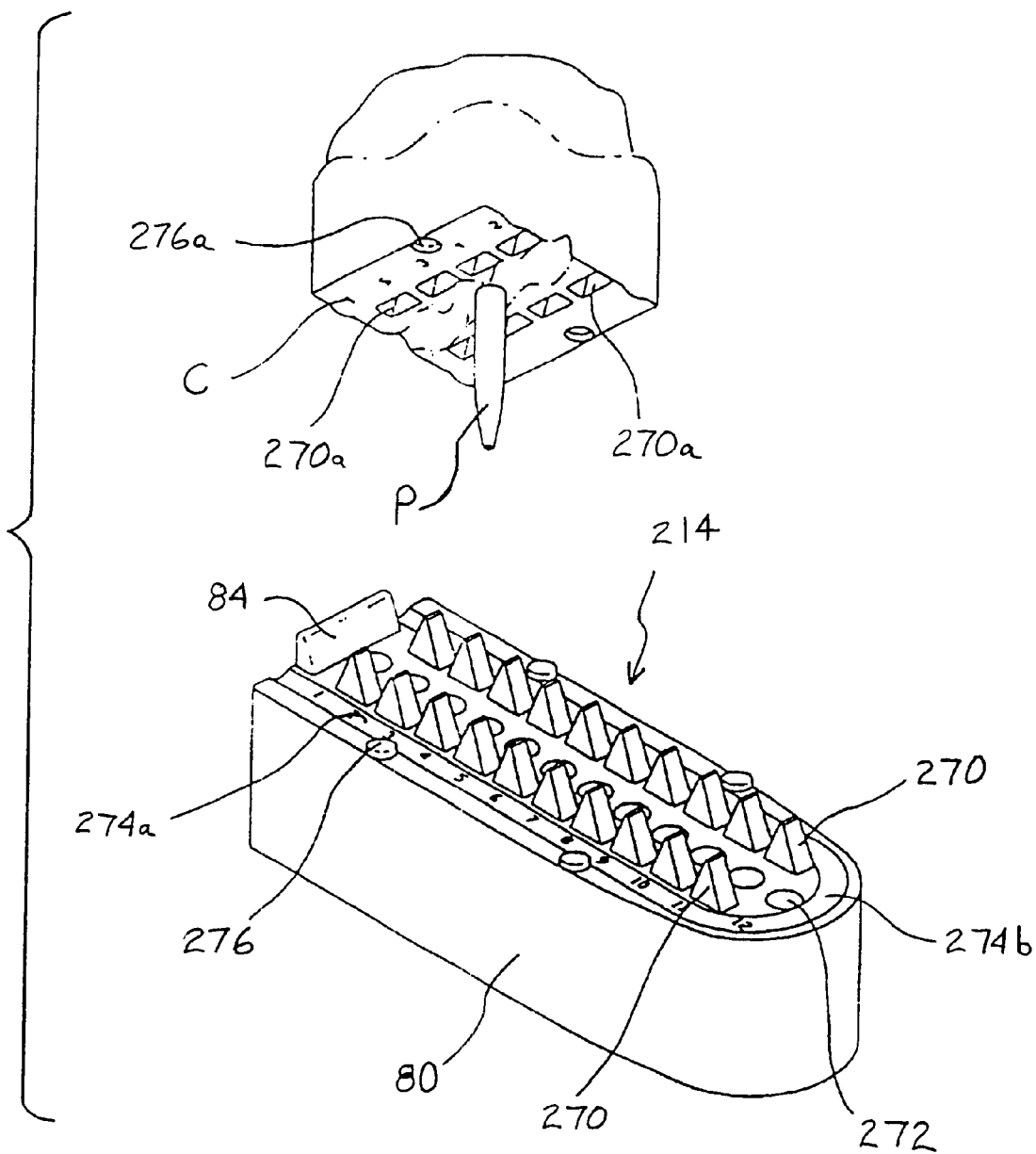
FIG. 30 is a perspective view of the support shown in FIG. 28, showing a segment of dental cast being re-registered therewith.

FIGS. 28–30 show a modified form of the quadrant support fully disclosed above with reference to FIGS. 7–11. The upper and lower supports 214, 216 shown in FIGS. 28–30 incorporate many of the features of the support 14, 16 shown in FIGS. 7–11. Accordingly, like reference numerals have been used to designate same or corresponding elements. However, as shown for example in FIG. 30, the arrangement of the registration pins 270, the holes 272 and the groove 274 of the support 214 have been modified. However, the remaining features of the support 214 are substantially the same as those described in detail in the forgoing description of the support 14 shown in FIGS. 7–11, and it should be understood that such foregoing description is equally applicable to the modified support 214 shown in FIGS. 28–30.

As shown for example in FIGS. 28 and 30, the support 214 includes two parallel rows of registration pins 270 extending upwardly from the upper surface 218. The registration pins 270 are evenly spaced apart and aligned in two rows extending along each side of a central longitudinal axis of the support 214. However, the support 214 may be configured such that the registration pins 270 are unevenly spaced apart, or may be arranged in rows which are not parallel or straight. The registration pins 270 taper inwardly proceeding in a direction away from the upper surface of the support 214. Preferably, the registration pins 270 are formed as pyramidal elements with the top portion thereof removed to form truncated pyramids, and each of the sides of the registration pins 270 is a flat, planar side. The registration pins 270 extend to a height which is greater that the height of the registration pins 70 shown in FIG. 8, and the amount of truncation is less such that the registration pins 270 are somewhat pointier than the registration pins 70 shown in FIG. 8.

In the embodiment disclosed, a first pair of the sides of the registration pins 270 taper inwardly at a first angle, and a second opposing pair of the sides of the registration pins 270 taper inwardly at a second angle different from the first angle. The registration pins 270 have a rectangular base with a length dimension extending along a longitudinal axis of the main body, and a width dimension extending transversely to the longitudinal axis. In this embodiment shown in FIGS. 28–30, the registration pins 270 have a height dimension which is greater than the length dimension and the width dimension. Preferably, adjacent ones of the registration pins 270 are spaced-apart from one another by a distance less than the length dimension of the base of the registration pins 270.

Located between the two rows of the registration pins 270 is a row of holes 272. The holes 272 are also evenly spaced and arranged in a row extending along the central longitudinal axis of the support 214 and parallel to the rows of registration pins 270. However, other arrangements of the holes 272 may be made other than the one parallel row of evenly spaced holes 272, as set forth herein. The holes 272 are circular in cross-section and taper inwardly extending into the main body 216 from the upper surface 218.

Located outwardly of the registration pins 270 is a groove 274 formed by a pair of straight groove portions 274a extending parallel to the rows of registration pins 270 which are interconnected by a semi-circular curved groove portion 274b. A sequence of numbers are located along the support 214, preferably being located within or near the groove 274. A plurality of circular protuberances 276 extend upwardly from the upper surface 18 at the edge thereof and outwardly of the straight groove portions 274a. As shown in FIG. 30, the registration pins 270 and the circular protuberances 276 form correspondingly shaped sockets 270a and 276a in the dental cast C.

Referring now to FIGS. 28–32, 36 and 37, the articulator arms 22, 24 shown therein incorporate many of the features of the articulator arms 22, 24 shown in FIGS. 3–6. Accordingly, like reference numerals have been used to designate same or corresponding elements. However, as shown for example in FIG. 32, the hinge portion 26 of the articulator arms 22, 24 has been modified to eliminate the stop portion 50, and the single glue slot 58 has been formed into three distinct glue slot segments 58. Also, the thickness and cross-sectional shape of the first cross member 30 has been modified to be thicker and to includes an arcuate portion facing the hinge 26. However, the remaining features of the articulator arms 22, 24 are substantially the same as those described in detail in the forgoing description of the articulator arms 22, 24 shown in FIGS. 3–6, and it should be understood that such foregoing description is equally applicable to the modified articulator arms 22, 24 shown in FIGS. 28–32, 36 and 37.

FIGS. 31–36 show a modified form of the full arch support fully disclosed above with reference to FIGS. 26 and 27. The upper and lower supports 370 shown in FIGS. 31–36 incorporate many of the features of the support 170 shown in FIGS. 26 and 27. Accordingly, like reference numerals have been used to designate same or corresponding elements. However, as shown for example in FIG. 31, the arrangement of the registration pins 372, the holes 374 and the groove 376 of the support 370 have been modified. Also, the ball and socket connection has been utilized between the support 370 and the articulator arm 22. However, the remaining features of the support 370 are substantially the same as those described in detail in the forgoing description of the support 170 shown in FIGS. 26 and 27, and it should be understood that such foregoing description is equally applicable to the modified support 370 shown in FIGS. 31–36.

Figure 31:
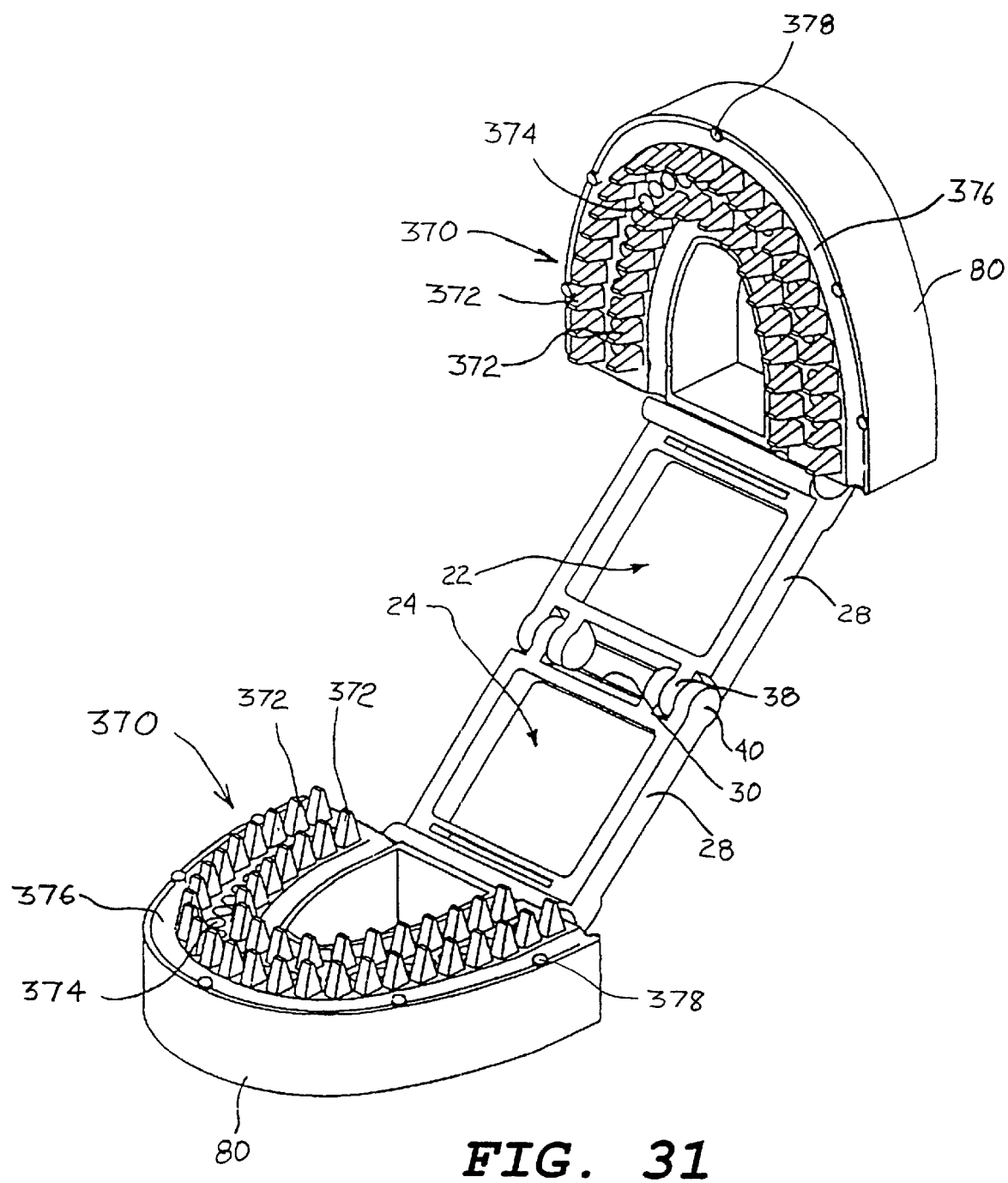
FIG. 31 is a perspective view of a modified form of the full arch dental articulator shown in FIG. 26.

As shown for example in FIG. 31, the support 370 includes two rows of registration pins 372 extending upwardly from the upper surface. The registration pins 372 are evenly spaced apart and aligned in two rows extending along each side of a central arcuate axis of the support 370. However, the support 370 may be configured such that the registration pins 372 are unevenly spaced apart, or may be arranged in rows which are not parallel or straight. The registration pins 372 taper inwardly proceeding in a direction away from the upper surface of the support 370. Preferably, the registration pins 372 are formed as pyramidal elements with the top portion thereof removed to form truncated pyramids, and each of the sides of the registration pins 372 is a flat, planar side. The registration pins 372 extend to a height which is greater that the height of the registration pins 70 shown in FIG. 8, and the amount of truncation is less such that the registration pins 372 are somewhat pointier than the registration pins 70 shown in FIG. 8.

In the embodiment disclosed, a first pair of the sides of the registration pins 372 taper inwardly at a first angle, and a second opposing pair of the sides of the registration pins 372 taper inwardly at a second angle different from the first angle. The registration pins 372 have a rectangular base with a length dimension extending in the same direction as a longitudinal axis of the main body, and a width dimension extending transversely to the longitudinal axis. In this embodiment shown in FIGS. 31–36, the registration pins 372 have a height dimension which is greater than the length dimension and the width dimension. Preferably, adjacent ones of the registration pins 372 are spaced-apart from one another by a distance less than the length dimension of the base of the registration pins 372.

Located between the two rows of the registration pins 372 is a row of holes 374. The holes 374 are also evenly spaced and arranged in a row extending along the central arcuate axis of the support 370 and between the rows of registration pins 372. However, other arrangements of the holes 374 may be made other than the one row of evenly spaced holes 374, as set forth herein. The holes 374 are circular in cross-section and taper inwardly extending into the support 370 for receiving a pin P therein.

Located outwardly and inwardly of the registration pins 372 are grooves 376, 377 which are arcuate in shape and follow the arcuate contour of the full arch support 370. A plurality of circular protuberances 378 extend upwardly from the upper surface at the edge thereof near the groove 376.

Figure 34:
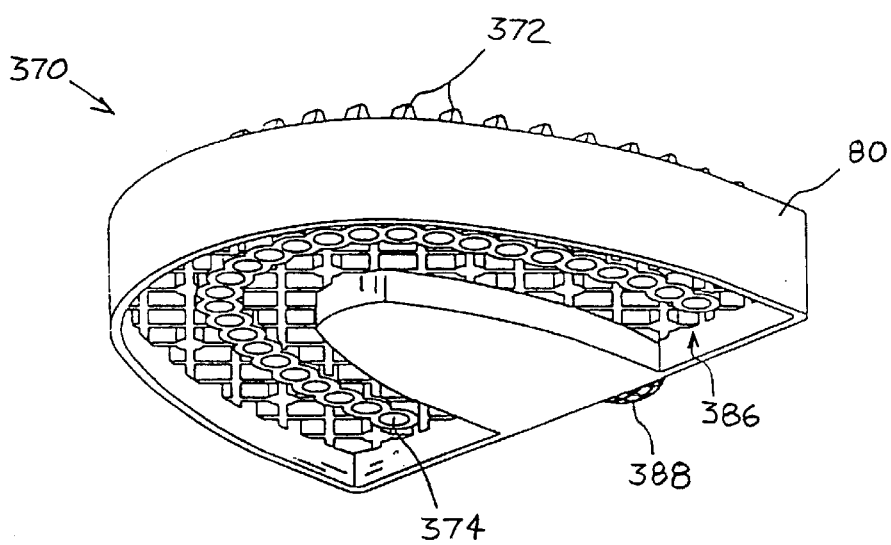
FIG. 34 is a perspective view of the bottom of the full arch support of FIG. 31.

The lower surface of the main body includes a cavity 386 therein. The holes 374 extend through the support 370 and terminate with openings in the cavity 386 as shown in FIG. 34.

Figure 32:
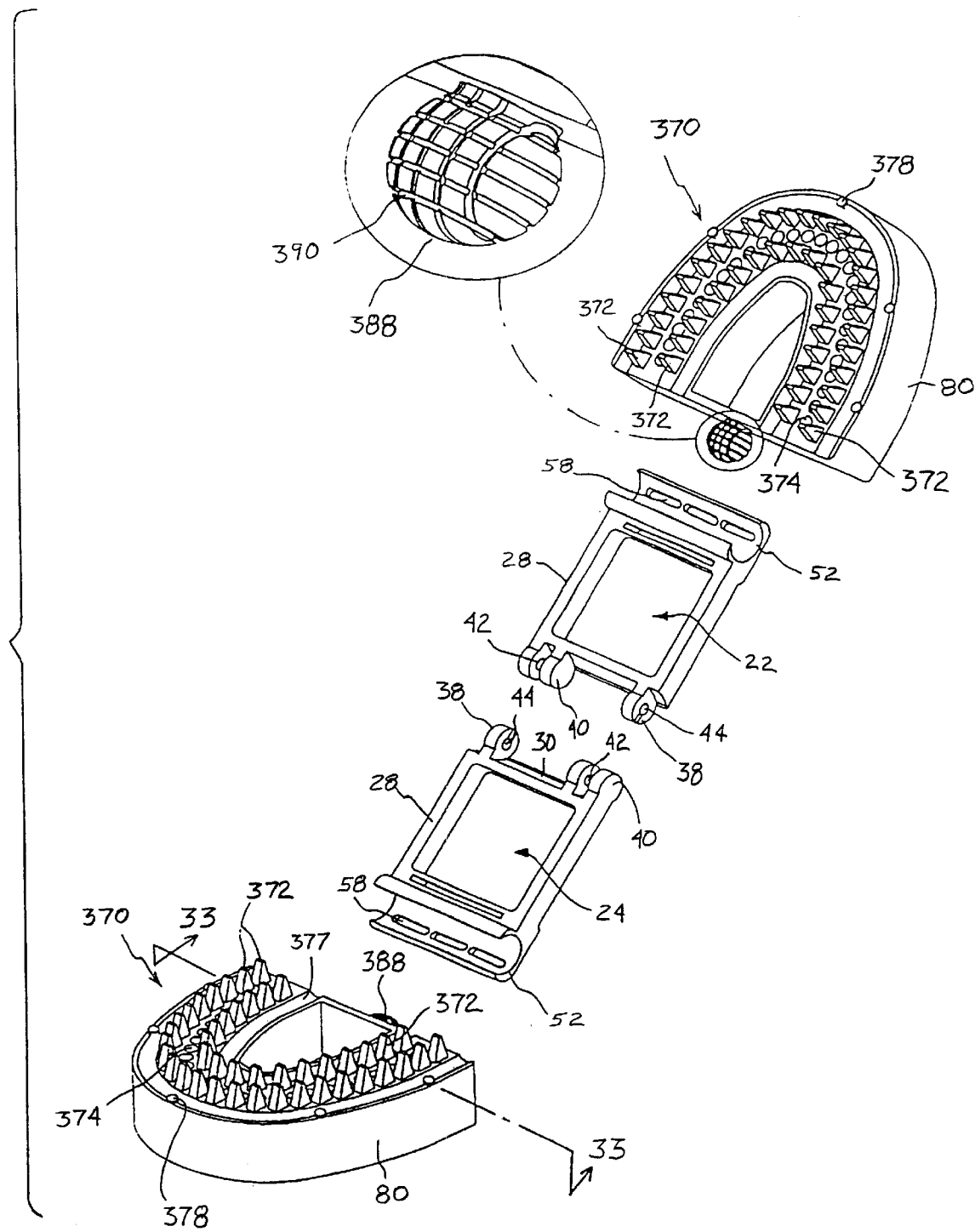
FIG. 32 is an exploded view of the full arch dental articulator of FIG. 31, including an enlarged view of the part-spherical attachment ball.
Figure 33:
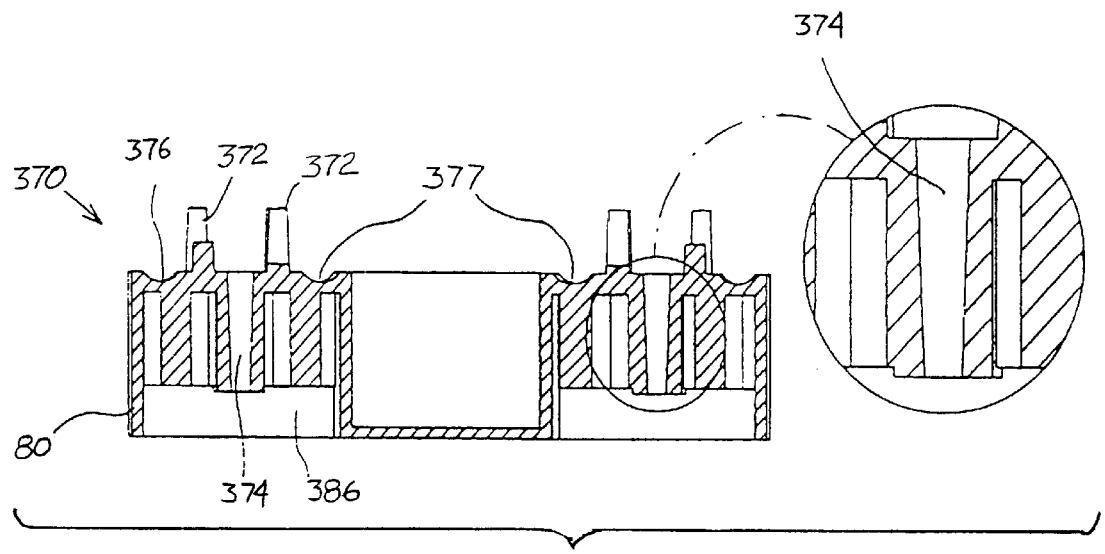
FIG. 33 is a cross sectional view taken along lines 33—33 in FIG. 32.

Referring now to FIG. 32, the rear wall of the support 370 includes an attachment ball 388 thereon. The attachment ball 388 is formed of a part spherical member connected to the rear wall. The attachment ball 388 includes a plurality of grooves 390 extending into the surface of the attachment ball 388. The grooves 390 extend either partially or fully circumferentially around each attachment ball 388, and the grooves 390 may intersect with one another, as shown in the enlarged portion of FIG. 32. The attachment ball 388 is inserted into the elongated part-cylindrical surface 54 of the socket member 52 of the articulator arm 22 in the manner previously described. It should be understood that instead of using the ball 388 and socket 52 joint, the full arch support 370 may be integrally formed with the articulator 22 as a one-piece unitary member like that shown in FIG. 26.

Figure 35:
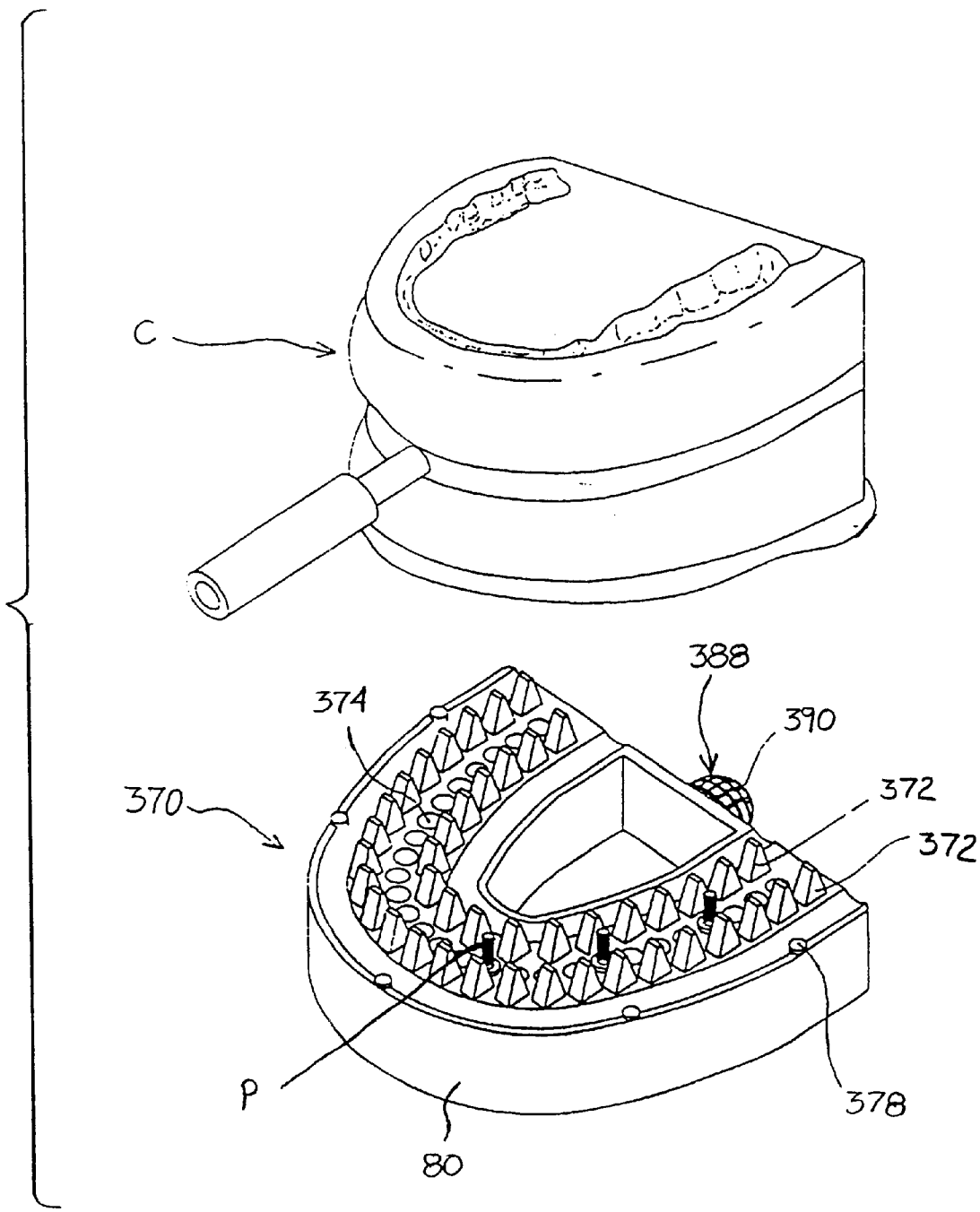
FIG. 35 is a perspective view showing a dental cast to be placed on the full arch support.
Figure 36:
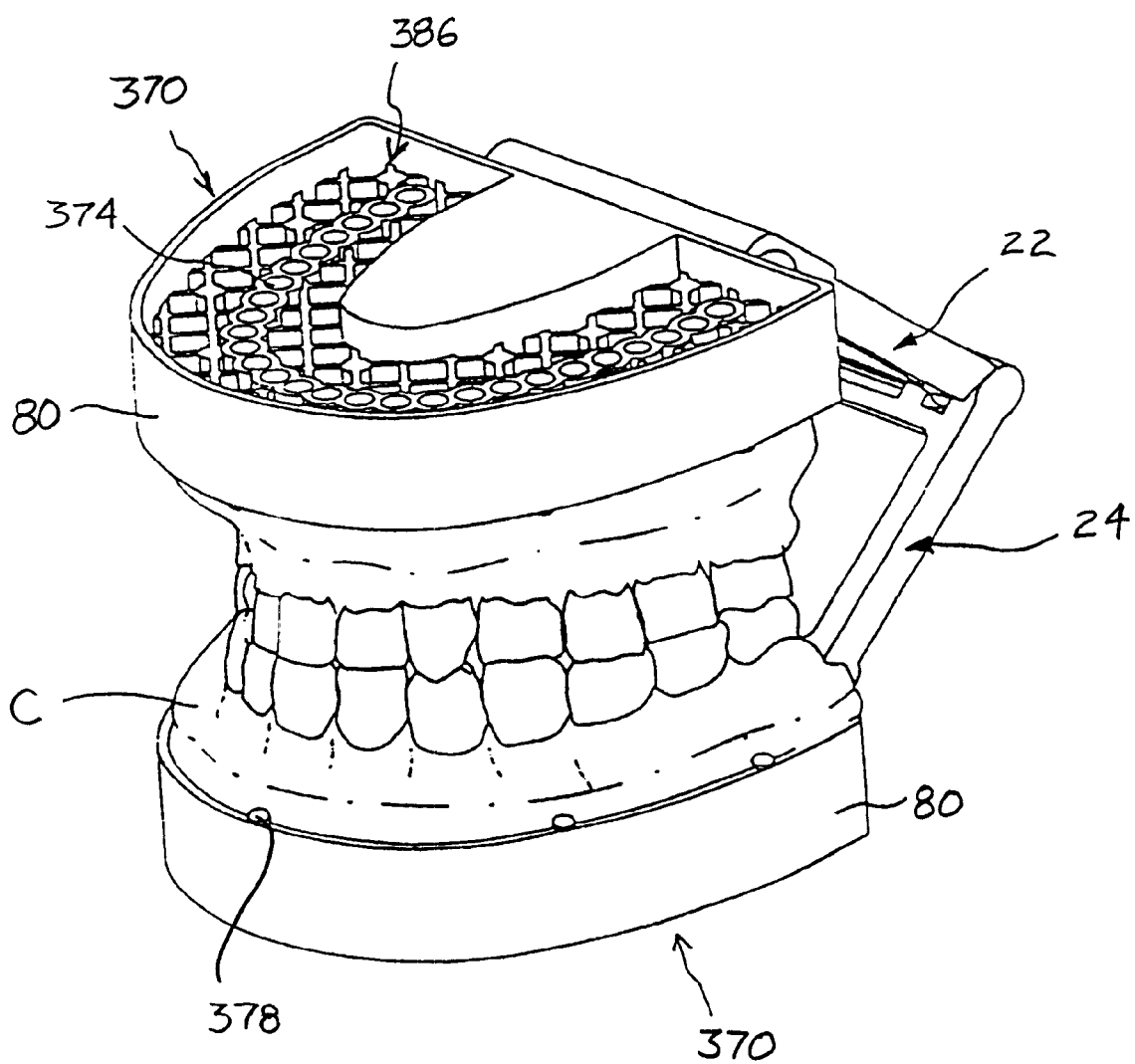
FIG. 36 is a perspective view of the articulated full arch support with a dental cast supported thereon.

FIG. 35 shows a dental cast C which is to be placed on the upper surface of the support 370, and FIG. 36 shows the completed assembly of the dental cast C, the upper and lower full arch supports 370, and the articulator arms 22, 24.

Figure 37:
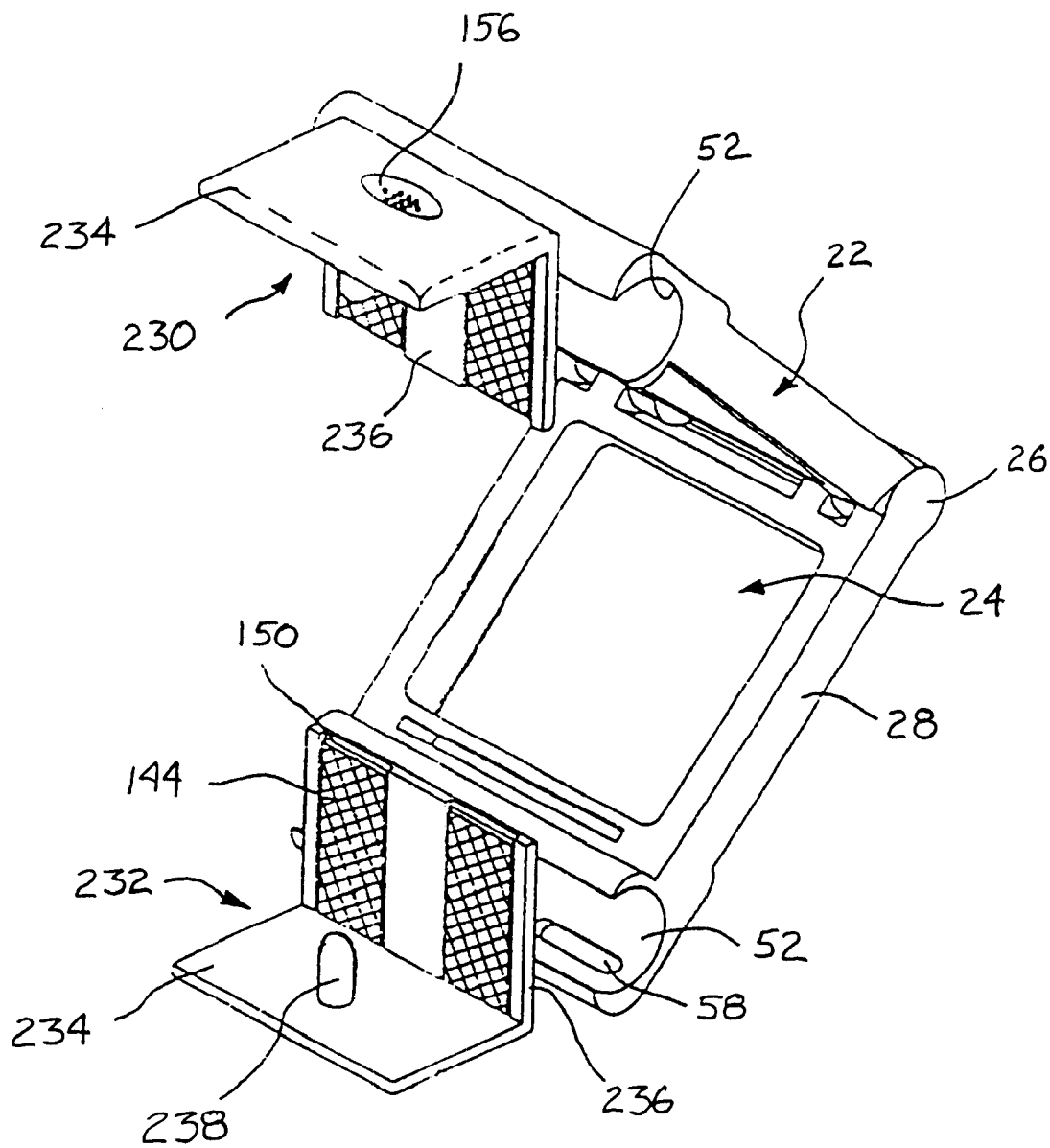
FIG. 37 is a perspective view of a modified form of the support shown in FIG. 19.
Figure 38:
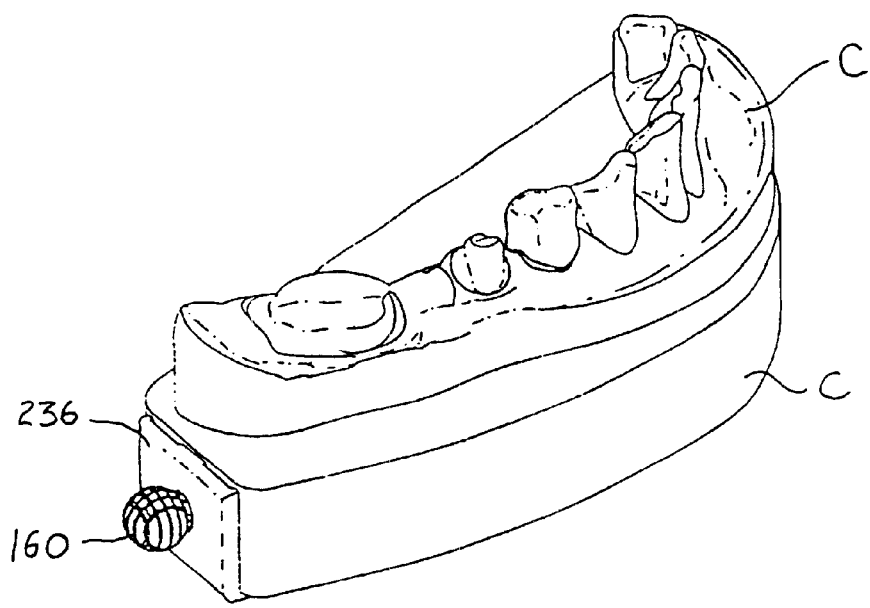
FIG. 38 is a perspective view of the support of FIG. 37 with a dental cast secured thereon.

FIGS. 37 and 38 show a modified form of the L-shaped support fully disclosed above with reference to FIGS. 19–25. The upper and lower L-shaped supports 230, 232 shown in FIGS. 37 and 38 incorporate many of the features of the support 130, 132 shown in FIGS. 19–25. Accordingly, like reference numerals have been used to designate same or corresponding elements. However, as shown for example in FIG. 37, the inside surfaces of the bottom member 234 and the back member 236 have been modified. However, the remaining features of the support 230 are substantially the same as those described in detail in the forgoing description of the support 130 shown in FIGS. 19–25, and it should be understood that such foregoing description is equally applicable to the modified support 230 shown in FIGS. 37 and 38.

The bottom member 234 includes a dowel 238 extending upwardly therefrom, which may protrude or embed into a dental cast C placed on the support 230. The dowel 238 is preferably cylindrical having a circular cross section and a constant diameter, although other cross sections and a tapered dowel are envisioned. Also, although only one dowel 238 is shown in the drawings, it is envisioned that two or more dowels may also be utilized.

The back member 236 includes a modified arrangement of the glue mesh which aids in the securement of a dental cast C to the support 230. Other arrangements of the inner surface of the back member 236 have been conceived, such as an inner surface having a plurality of vertically extending grooves therein (not shown). Approximately five grooves would be used, and the grooves would preferably be parallel with one another, and may vary in width, becoming narrower as each groove approaches the bottom member 234.

Figure 39:
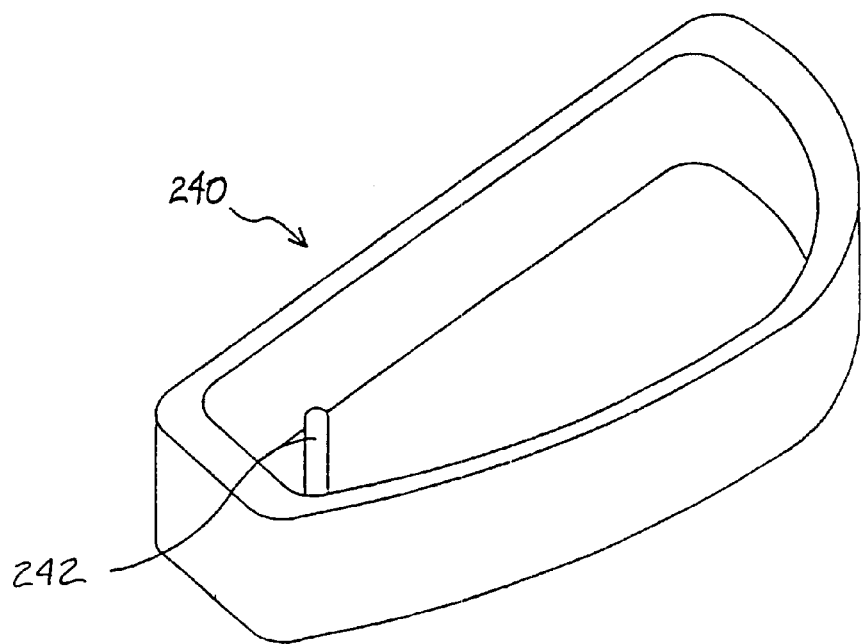
FIG. 39 is a perspective view of a mold for forming a lower portion of the dental cast which is compatible with the support of FIG. 37.

FIG. 39 shows a mold 240 which may be utilized to form the lower portion of a dental cast C which is compatible with the L-shaped support 230. The mold 240 includes a dowel 242 extending upwardly from the bottom of the mold 240. Casting material would be poured into the mold 240 while in a viscous state and allowed to harden. Due to the presence of the dowel 242 in the mold 240, a correspondingly shaped aperture would be formed in the hardened dental cast C. Thereafter, upon placement of the dental cast C onto the L-shaped support 230, the dowel 238 of the L-shaped support 230 would penetrate into the aperture in the dental casting C.

In the present invention, because the registration pins 70, 172, 270, 372 provide sufficient registration of the dental cast C with respect to the main body 16, it is not essential that additional pins be embedded into the dental cast which would be inserted into the holes 72. This is beneficial, for example, in the instance where ceramic crowns are being formed. To make a ceramic crown, the segmented portion of the dental cast having the crown material thereon is placed in a refractory oven at a temperature of approximately 1400° Fahrenheit. At this temperature, pins formed of standard metals will melt, and therefore it is necessary to use refractory pins which are very expensive. Therefore, because the present invention may be practiced without the utilization of additional pins, it is possible to form ceramic crowns without requiring the added expense of utilizing refractory pins.

In the present invention, the registration pins 70, 172, 270, 372 permit proper registration of a segment of the dental cast on the support even if only one registration pin is embedded into the segment. This is due in part to the non-rotational property of the registration pins with respect to the segment. Although the pyramid shape disclosed herein is preferred, other shapes are possible, such as triangular, hexagonal or any polygonal shape, ovals, semicircles, crescents, hearts, clovers, stars, or any non-circular cross section. However, more complex shapes become more difficult to manufacture, and therefore the simpler non-circular shapes are preferred.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dental modeling system comprising:
   a support for a dental cast, said support including:
      a main body having a top surface; and
      a plurality of registration pins extending upwardly from said top surface, said registration pins each having a pyramidal shape with four sides which taper inwardly extending away from said top surface of said main body;
   an articulator arm attached to said support; and
   a joint located between said articulator arm and said support, said joint including:
      an elongated part-cylindrical concave socket member; and
      a part-spherical ball received within said socket member.

2. The dental modeling system according to claim 1, wherein each of said sides of said registration pins is flat.

3. The dental modeling system according to claim 1, wherein said registration pins have a rectangular base with a length dimension and a width dimension.

4. The dental modeling system according to claim 3, wherein adjacent ones of said registration pins are spaced apart from one another by a distance less than said length dimension and said width dimension of said base.

5. The dental modeling system according to claim 3, wherein said registration pins have a height dimension which is greater than said length dimension and said width dimension.

6. The dental modeling system according to claim 1, wherein a first one of said sides of said registration pins tapers inwardly at a first angle, and a second one of said sides of said registration pins tapers inwardly at a second angle different from said first angle.

7. The dental modeling system according to claim 1, wherein a first opposing pair of said sides of said registration pins taper inwardly at a first angle, and a second opposing pair of said sides of said registration pins taper inwardly at a second angle different from said first angle.

8. The dental modeling system according to claim 1, wherein said registration pins are arranged in at least one row extending along a longitudinal axis of said main body.

9. The dental modeling system according to claim 8, wherein said row is straight and said registration pins are aligned in said row.

10. The dental modeling system according to claim 8, wherein said registration pins have a base with a length dimension extending along said longitudinal axis of said main body.

11. The dental modeling system according to claim 10, wherein adjacent ones of said registration pins are spaced a part from one another by a distance less than said length dimension of said base.

12. The dental modeling system according to claim 1, wherein said registration pins are arranged in at least two spaced-apart rows.

13. The dental modeling system according to claim 12, wherein said rows are parallel with one another.

14. The dental modeling system according to claim 1, wherein said registration pins are arranged in at least one row curved in an arch extending along said main body.

15. The dental modeling system according to claim 1, further comprising at least one aperture located in said top surface and extending into said main body.

16. The dental modeling system according to claim 15, wherein a bottom portion of said main body includes a cavity located therein extending into said main body, said at least one aperture extending through said main body and opening into said cavity.

17. The dental modeling system according to claim 1, further comprising a plurality of apertures located in said top surface and extending into said main body.

18. The dental modeling system according to claim 17, wherein said registration pins are aligned in at least one row extending along a longitudinal axis of said main body, and said plurality of apertures are aligned in at least two spaced-apart parallel rows extending along each side of said row of registration pins.

19. The dental modeling system according to claim 17, wherein said plurality of apertures are aligned in at least one row extending along a logitudinal axis of said main body, and said registration pins are aligned in at least two spaced-apart parallel rows extending along each side of said row of apertures.

20. The dental modeling system according to claim 1, wherein said articulator arm comprises a first articulator arm having a first end and a second end, said first end including a first hinge portion; and a first pair of spaced-apart arm members; and further comprising:

a second articulator arm having a first end and a second end, said first end including a second hinge portion; and a second pair of spaced-apart arm members, said second hinge portion of said second articulator arm being pivotally connected to said first hinge portion of said first articulator arm.

21. The dental modeling system according to claim 1, wherein said joint provides four degrees of freedom of movement of said main body with respect to said articulator arm.

22. The dental modeling system according to claim 21, wherein said four degrees of freedom of movement include three degrees of rotation about mutually orthogonal axes, and one degree of translation along one of said axes.

23. The dental modeling system according to claim 1, wherein said part-spherical ball is attached to a rear wall of said main body, and said elongated part-cylindrical concave socket member is attached to said articulator arm.

24. The dental modeling system according to claim 1, wherein said main body further comprises a rear wall, and said top surface includes a blocking member extending upwardly therefrom adjacent said rear wall.

25. The dental modeling system according to claim 1, wherein the main body further comprises a pair of side walls which taper inwardly from said top surface toward a bottom surface of said main body.

26. The dental modeling system according claim 1, wherein said registration pins have a truncated top portion such that said registration pins are shaped as truncated pyramids.

27. The dental modeling system according to claim 1, wherein said registration pins are formed integrally with said main body as a one-piece unit.

* * * * *